(12) United States Patent
Doxey et al.

(10) Patent No.: US 10,206,947 B2
(45) Date of Patent: *Feb. 19, 2019

(54) TOPICAL COMPOSITIONS AND METHODS OF USING THE SAME

(71) Applicant: Novan, Inc., Durham, NC (US)

(72) Inventors: Ryan Doxey, Raleigh, NC (US); Jian Bao, Cary, NC (US)

(73) Assignee: Novan, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/910,215

(22) PCT Filed: Jan. 27, 2015

(86) PCT No.: PCT/US2015/013043
§ 371 (c)(1),
(2) Date: Feb. 4, 2016

(87) PCT Pub. No.: WO2016/022170
PCT Pub. Date: Feb. 11, 2016

(65) Prior Publication Data
US 2016/0256484 A1     Sep. 8, 2016

Related U.S. Application Data

(63) Continuation-in-part of application No. PCT/US2014/050345, filed on Aug. 8, 2014.

(60) Provisional application No. 61/868,139, filed on Aug. 21, 2013, provisional application No. 61/863,541, filed on Aug. 8, 2013.

(51) Int. Cl.
| | |
|---|---|
| A61K 9/10 | (2006.01) |
| A61K 33/00 | (2006.01) |
| A61K 8/25 | (2006.01) |
| A61K 8/34 | (2006.01) |
| A61K 8/898 | (2006.01) |
| A61K 9/00 | (2006.01) |
| A61K 9/06 | (2006.01) |
| A61K 9/107 | (2006.01) |
| A61K 47/02 | (2006.01) |
| A61K 47/12 | (2006.01) |
| A61K 47/10 | (2017.01) |
| A61K 47/14 | (2017.01) |
| A61K 47/32 | (2006.01) |
| A61K 47/38 | (2006.01) |
| A61K 47/44 | (2017.01) |
| A61Q 17/00 | (2006.01) |
| A61Q 19/00 | (2006.01) |
| A61K 8/04 | (2006.01) |

(52) U.S. Cl.
CPC .......... *A61K 33/00* (2013.01); *A61K 8/042* (2013.01); *A61K 8/25* (2013.01); *A61K 8/345* (2013.01); *A61K 8/898* (2013.01); *A61K 9/0014* (2013.01); *A61K 9/06* (2013.01); *A61K 9/10* (2013.01); *A61K 9/107* (2013.01); *A61K 47/02* (2013.01); *A61K 47/10* (2013.01); *A61K 47/12* (2013.01); *A61K 47/14* (2013.01); *A61K 47/32* (2013.01); *A61K 47/38* (2013.01); *A61K 47/44* (2013.01); *A61Q 17/005* (2013.01); *A61Q 19/00* (2013.01); *A61K 2800/22* (2013.01)

(58) Field of Classification Search
None
See application file for complete search history.

(56) References Cited

U.S. PATENT DOCUMENTS

| | | |
|---|---|---|
| 3,754,368 A | 8/1973 | Moore et al. |
| 4,182,827 A | 1/1980 | Jones et al. |
| 4,829,092 A | 5/1989 | Nelson et al. |
| 4,917,886 A | 4/1990 | Asche et al. |
| 5,405,919 A | 4/1995 | Keefer |
| 5,519,020 A | 5/1996 | Smith et al. |
| 5,691,423 A | 11/1997 | Smith et al. |
| 5,770,645 A | 6/1998 | Stamler et al. |
| 5,814,656 A | 9/1998 | Saavedra et al. |
| 5,814,666 A | 9/1998 | Green et al. |
| 5,840,759 A | 11/1998 | Mitchell et al. |
| 5,910,316 A | 6/1999 | Keefer et al. |
| 5,958,427 A | 9/1999 | Salzman et al. |
| 5,968,001 A | 10/1999 | Freeman |
| 5,968,528 A | 10/1999 | Deckner et al. |
| 6,103,266 A | 8/2000 | Tapolsky et al. |
| 6,103,275 A | 8/2000 | Seitz et al. |
| 6,110,453 A | 8/2000 | Keefer et al. |
| 6,303,141 B1 | 10/2001 | Fischer et al. |
| 6,319,913 B1 | 11/2001 | Mak et al. |
| 6,382,526 B1 | 5/2002 | Reneker et al. |
| 6,465,445 B1 | 10/2002 | Labrie |
| 6,479,058 B1 | 11/2002 | McCadden |

(Continued)

FOREIGN PATENT DOCUMENTS

| | | |
|---|---|---|
| CA | 2 594 407 A1 | 8/2006 |
| EP | 1 300 424 A1 | 4/2003 |

(Continued)

OTHER PUBLICATIONS

U.S. Appl. No. 14/133,973, Kougoulos et al., filed Dec. 19, 2013.

(Continued)

*Primary Examiner* — Jessica Worshaw
(74) *Attorney, Agent, or Firm* — Myers Bigel, P.A.

(57) ABSTRACT

The present invention generally relates to topical compositions and methods of using the same. The topical compositions may comprise a hydrophilic composition and a hydrophobic composition in admixture. The hydrophobic composition may include a nitric oxide-releasing compound such as, for example, a diazeniumdiolate functionalized co-condensed silica particle. In some embodiments, the topical composition may be self-emulsifying. Further described herein are kits comprising a hydrophilic composition and a hydrophobic composition.

22 Claims, 11 Drawing Sheets

(56) References Cited

U.S. PATENT DOCUMENTS

| | | |
|---|---|---|
| 6,520,425 B1 | 2/2003 | Reneker |
| 6,695,992 B2 | 2/2004 | Reneker |
| 6,719,997 B2 | 4/2004 | Hsu et al. |
| 6,737,447 B1 | 5/2004 | Smith et al. |
| 6,818,018 B1 | 11/2004 | Sawhney |
| 6,861,064 B1 | 3/2005 | Laakso et al. |
| 7,048,951 B1 | 5/2006 | Seitz et al. |
| 7,704,518 B2 | 4/2010 | Tamarkin et al. |
| 8,241,650 B2 | 8/2012 | Peters |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,486,451 B2 | 7/2013 | Morris et al. |
| 8,591,876 B2 | 11/2013 | Bauman et al. |
| 8,617,100 B2 | 12/2013 | Eini et al. |
| 8,636,982 B2 | 1/2014 | Tamarkin et al. |
| 8,722,103 B2 | 5/2014 | Morris et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 9,101,662 B2 | 8/2015 | Tamarkin et al. |
| 9,161,916 B2 | 10/2015 | Tamarkin et al. |
| 9,265,725 B2 | 2/2016 | Tamarkin et al. |
| 9,320,705 B2 | 4/2016 | Tamarkin et al. |
| 2002/0012816 A1 | 1/2002 | Shimizu et al. |
| 2002/0013304 A1 | 1/2002 | Wilson et al. |
| 2002/0028223 A1 | 3/2002 | Vatter et al. |
| 2002/0082221 A1 | 6/2002 | Herrmann et al. |
| 2002/0094985 A1 | 7/2002 | Herrmann et al. |
| 2002/0122771 A1 | 9/2002 | Holland et al. |
| 2002/0136750 A1 | 9/2002 | Benjamin et al. |
| 2002/0155174 A1 | 10/2002 | Benjamin et al. |
| 2003/0077243 A1 | 4/2003 | Fitzhugh |
| 2003/0159702 A1 | 8/2003 | Lindell et al. |
| 2003/0175328 A1 | 9/2003 | Shefer et al. |
| 2003/0205234 A1 | 11/2003 | Bardach et al. |
| 2003/0235605 A1 | 12/2003 | Lelah et al. |
| 2004/0009238 A1 | 1/2004 | Miller et al. |
| 2004/0043068 A1 | 3/2004 | Tedeschi et al. |
| 2004/0068005 A1 | 4/2004 | Szilvassy et al. |
| 2004/0171589 A1 | 9/2004 | Herrmann et al. |
| 2004/0202684 A1 | 10/2004 | Djerassi |
| 2004/0220260 A1 | 11/2004 | Cals-Grierson |
| 2004/0265244 A1 | 12/2004 | Rosen |
| 2005/0038473 A1 | 2/2005 | Tamarkin et al. |
| 2005/0232869 A1 | 10/2005 | Tamarkin et al. |
| 2005/0271596 A1 | 12/2005 | Friedman et al. |
| 2006/0159734 A1 | 7/2006 | Shudo |
| 2006/0160897 A1 | 7/2006 | Pelicci et al. |
| 2006/0173076 A1 | 8/2006 | Vishnupad et al. |
| 2006/0269620 A1 | 11/2006 | Morris et al. |
| 2006/0275218 A1 | 12/2006 | Tamarkin et al. |
| 2007/0166255 A1 | 7/2007 | Gupta |
| 2007/0243224 A1 | 10/2007 | Ludwig et al. |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0069779 A1 | 3/2008 | Tamarkin et al. |
| 2008/0071206 A1 | 3/2008 | Peters |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311163 A1 | 12/2008 | Peters |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0068248 A1 | 3/2009 | Waterhouse et al. |
| 2009/0130029 A1 | 5/2009 | Tamarkin et al. |
| 2009/0175799 A1 | 7/2009 | Tamarkin et al. |
| 2009/0214618 A1 | 8/2009 | Schoenfisch et al. |
| 2009/0226380 A1 | 9/2009 | Clark et al. |
| 2009/0297634 A1 | 12/2009 | Friedman et al. |
| 2010/0015253 A1 | 1/2010 | Benjamin |
| 2010/0098733 A1 | 4/2010 | Stasko |
| 2010/0221195 A1 | 9/2010 | Tamarkin et al. |
| 2010/0266510 A1 | 10/2010 | Tamarkin et al. |
| 2010/0286285 A1 | 11/2010 | Barthez et al. |
| 2010/0310476 A1 | 12/2010 | Tamarkin et al. |
| 2010/0331968 A1 | 12/2010 | Morris et al. |
| 2011/0027369 A1 | 2/2011 | Franke |
| 2011/0045037 A1 | 2/2011 | Tamarkin et al. |
| 2011/0052650 A1 | 3/2011 | Morris et al. |
| 2011/0082167 A1 | 4/2011 | Pisak et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2011/0263526 A1 | 10/2011 | Satyam |
| 2012/0114547 A1 | 5/2012 | Smith |
| 2012/0134951 A1 | 5/2012 | Stasko et al. |
| 2012/0136323 A1 | 5/2012 | Stasko et al. |
| 2012/0141384 A1 | 6/2012 | Tamarkin et al. |
| 2012/0156163 A1 | 6/2012 | Bauman et al. |
| 2012/0237453 A1 | 9/2012 | Tamarkin et al. |
| 2013/0059017 A1 | 3/2013 | Perricone et al. |
| 2013/0109756 A1 | 5/2013 | Huber et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0310533 A1 | 11/2013 | Bao et al. |
| 2013/0344334 A1 | 12/2013 | Schoenfisch et al. |
| 2014/0017121 A1 | 1/2014 | Schoenfisch et al. |
| 2014/0057001 A1 | 2/2014 | Bauman et al. |
| 2014/0058124 A1 | 2/2014 | Schoenfisch et al. |
| 2014/0065200 A1 | 3/2014 | Schoenfisch et al. |
| 2014/0107071 A1 | 4/2014 | Kougoulos et al. |
| 2014/0134321 A1 | 5/2014 | Stasko et al. |
| 2014/0171395 A1 | 6/2014 | Schoenfisch et al. |
| 2014/0193502 A1 | 7/2014 | Tamarkin et al. |
| 2014/0242023 A1 | 8/2014 | Doxey et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2014/0369949 A1 | 12/2014 | Peters |
| 2015/0017103 A1 | 1/2015 | Tamarkin et al. |
| 2015/0024052 A1 | 1/2015 | Doxey |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2015/0141606 A1 | 5/2015 | Bao et al. |
| 2015/0182543 A1 | 7/2015 | Schoenfisch et al. |
| 2015/0225488 A1 | 8/2015 | Schoenfisch et al. |
| 2016/0008275 A1 | 1/2016 | Doxey et al. |

FOREIGN PATENT DOCUMENTS

| | | |
|---|---|---|
| EP | 1 707 224 A1 | 10/2006 |
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| GB | 2 354 441 | 3/2001 |
| JP | 03-044396 | 2/1991 |
| JP | H07-039748 | 2/1995 |
| JP | 2003-212773 | 7/2003 |
| JP | 2003-286153 | 10/2003 |
| JP | 2012-197300 | 10/2012 |
| WO | WO 93/10754 A1 | 6/1993 |
| WO | WO 94/08603 A1 | 4/1994 |
| WO | WO 96/13164 A1 | 5/1996 |

(56) References Cited

FOREIGN PATENT DOCUMENTS

| | | |
|---|---|---|
| WO | WO 96/15797 A1 | 5/1996 |
| WO | WO 98/05689 A1 | 2/1998 |
| WO | WO 00/49993 A2 | 8/2000 |
| WO | WO 01/21148 A1 | 3/2001 |
| WO | WO 01/26702 A2 | 4/2001 |
| WO | WO 01/85013 A2 | 11/2001 |
| WO | WO 02/020026 A2 | 3/2002 |
| WO | WO 02/41902 A1 | 5/2002 |
| WO | WO 02/056864 A2 | 7/2002 |
| WO | WO 03/013489 A1 | 2/2003 |
| WO | WO 03/072039 A2 | 9/2003 |
| WO | WO 03/078437 A1 | 9/2003 |
| WO | WO 03/086282 A2 | 10/2003 |
| WO | WO 03/092763 A1 | 11/2003 |
| WO | WO 2004/012659 A2 | 2/2004 |
| WO | WO 2004/012874 A1 | 2/2004 |
| WO | WO 2004/098538 A2 | 11/2004 |
| WO | WO 2005/003032 A1 | 1/2005 |
| WO | WO 2005/004984 A1 | 1/2005 |
| WO | WO 2005/011575 A2 | 2/2005 |
| WO | WO 2005/037339 A1 | 4/2005 |
| WO | WO 2005/046661 A2 | 5/2005 |
| WO | WO 2006/084910 A2 | 8/2006 |
| WO | WO 2006/084912 A1 | 8/2006 |
| WO | WO 2006/100154 A1 | 9/2006 |
| WO | WO 2006/128121 A2 | 11/2006 |
| WO | WO 2006/138035 A1 | 12/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/094866 A1 | 8/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/067095 A1 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2009/131931 A1 | 10/2009 |
| WO | WO 2010/016686 A2 | 2/2010 |
| WO | WO 2011/005846 A1 | 1/2011 |
| WO | WO 2011/022652 A1 | 2/2011 |
| WO | WO 2011/022680 A2 | 2/2011 |
| WO | WO 2011/061519 A2 | 5/2011 |
| WO | WO 2011/073998 A1 | 6/2011 |
| WO | WO 2012/001403 A1 | 1/2012 |
| WO | WO 2012/035468 A2 | 3/2012 |
| WO | WO 2012/082976 A1 | 6/2012 |
| WO | WO 2012/100174 A1 | 7/2012 |
| WO | WO 2012/153331 A2 | 11/2012 |
| WO | WO 2013/006608 A1 | 1/2013 |
| WO | WO 2013/006613 A1 | 1/2013 |
| WO | WO 2013/138073 A1 | 9/2013 |
| WO | WO 2013/138075 A1 | 9/2013 |
| WO | WO 2015/021382 A2 | 2/2015 |
| WO | WO 2016/007834 A1 | 1/2016 |
| WO | WO 2016/010988 A1 | 1/2016 |
| WO | WO 2016/022170 A1 | 2/2016 |

OTHER PUBLICATIONS

U.S. Appl. No. 14/191,958, Doxey, filed Feb. 27, 2014.
U.S. Appl. No. 14/771,138, Doxey, filed Aug. 27, 2015.
Al-Sa'Doni et al. "S-Nitrosothiols: a class of nitric oxide-donor drugs" *Clinical Science* 98:507-520 (2000).
Hrabie et al. "Chemistry of the Nitric Oxide-Releasing Diazeniumdiolate ("Nitrosohydroxylamine") Functional Group and Its Oxygen-Substituted Derivatives" *Chemical Reviews* 102:1135-1154 (2002).
International Preliminary Report on Patentability corresponding to International Patent Application No. PCT/US2014/050345 (8 pages) (dated Feb. 18, 2016).
Pulfer et al. "Incorporation of nitric oxide-releasing crosslinked polyethyleneimine microspheres into vascular grafts" *Journal of Biomedical Materials Research* 37:182-189 (1997).
Sangster, James "Octanol-Water Partition Coefficients of Simple Organic Compounds" *Journal of Physical and Chemical Reference Data* 18(3):1111-1227 (1989).
Smith et al. "Transdermal delivery of nitric oxide from diazeniumdiolates" *Journal of Controlled Release* 51:153-159 (1998).
Wang et al. "Nitric Oxide Donors: Chemical Activities and Biological Applications" *Chemical Reviews* 102:1091-1134 (2002).
Boykin et al. "HBO Mediates Increased Nitric Oxide Production Associated With Wound Healing" *Wound Repaid and Regeneration* 12(2):A15 (Abstract 054) (2004).
Amadeu et al. "Nitric Oxide Donor Improves Healing if Applied on Inflammatory and Proliferative Phase" *Journal of Surgical Research* 149(1):84-93 (2008).
Bohl Masters et al. "Effects of nitric oxide releasing poly(vinyl alcohol) hydrogel dressings on dermal wound healing in diabetic mice" *Wound Repair and Regeneration* 10(5):286-294 (2002).
Hetrick et al. "Anti-biofilm efficacy of nitric oxide-releasing silica nanoparticles" *Biomaterials* 30(14):2782-2789 (2009).
International Search Report and the Written Opinion of the International Searching Authority corresponding to International Patent Application No. PCT/US2014/050345 (12 pages) (dated Nov. 14, 2014).
U.S. Appl. No. 15/156,889, Peters, filed May 17, 2016.
Extended European Search Report corresponding to European Patent Application No. 14835259.4 (6 pages) (dated Feb. 13, 2017).
International Search Report and the Written Opinion of the International Searching Authority corresponding to International Patent Application No. PCT/US2015/013043 (13 pages) (dated Apr. 15, 2015).
Kandavilli et al. "Polymers in Transdermal Drug Delivery Systems" *Pharmaceutical Technology* pp. 62-80 (2002).
Wang et al. "Nitric Oxide Donors: Chemical Activities and Biological Applications" *Chemical Reviews* 102(4):1091-1134 (2002).
Extended European Search Report corresponding to European Patent Application No. 15830341.2 (7 pages) (dated Mar. 21, 2018).
Office Action corresponding to Japanese Patent Application No. 2016-533467 (9 pages) (dated May 8, 2018).
Seta, Yasuo "Drug Design of Poorly Soluble Drug by Nanoparticle Formation Technology" *Pharmacia* 48(10):933-935 (2012).
Decision of Rejection corresponding to Japanese Patent Application No. 2016-533467 (11 pages) (dated Sep. 7, 2018).

A – 3.2% Nitricil™ NVN4

B – 9.73% Nitricil™ NVN4

C – 19.4% Nitricil™ NVN4

D – Vehicle

E – Mupirocin

F – Untreated Control

A – 3.2% Nitricil™ NVN4
B – 9.73% Nitricil™ NVN4
C – 19.4% Nitricil™ NVN4
D – Vehicle
E – Mupirocin
F – Untreated Control ○ = Oil droplets

US 10,206,947 B2

TOPICAL COMPOSITIONS AND METHODS OF USING THE SAME

RELATED APPLICATIONS

This application is a 35 U.S.C. § 371 national stage application of International Application No. PCT/US15/13043, filed Jan. 27, 2015, which is a continuation-in-part of International Application No. PCT/US2014/050345 filed on Aug. 8, 2014, which claims the benefit of and priority to U.S. Provisional Application Ser. No. 61/868,139 filed on Aug. 21, 2013 and U.S. Provisional Application Ser. No. 61/863,541 filed on Aug. 8, 2013, the disclosures of each of which are hereby incorporated by reference herein in their entirety.

STATEMENT OF GOVERNMENT SUPPORT

This invention was made with government support under Contract No. W81XWH-11-C-0029 awarded by the U.S. Department of Defense and Grant No. 5R43AI096569 awarded by the National Institutes of Health. The government has certain rights in the invention.

FIELD OF THE INVENTION

The present invention generally relates to topical compositions and methods of using the same.

BACKGROUND

Topical compositions that aid in wound healing, such as the rate of healing, may be desirable. However, determining topical compositions that can aid in wound healing can be challenging.

In addition, moisture sensitive active pharmaceutical ingredients (APIs) can present challenges when delivered topically. While the API may be incorporated in a hydrophobic topical composition so that it has suitable shelf life stability, this same stability may reduce the ability to deliver the drug if moisture is the activating agent.

The present invention may address previous shortcomings in the art by providing topical compositions and methods of using the same.

SUMMARY

A first aspect of the present invention comprises a topical composition comprising a hydrophilic composition and a hydrophobic composition in admixture. In some embodiments, the topical composition further comprises a nitric oxide-releasing active pharmaceutical ingredient.

A second aspect of the present invention comprises a composition comprising: a hydrophobic base; at least one of an amphiphilic compound or an emulsifying agent; a polymer; a polyhydric alcohol; and water. In some embodiments, the composition further comprises a cosolvent. In some embodiments, the composition further comprises a nitric oxide-releasing active pharmaceutical ingredient. In some embodiments, the composition further comprises a buffer and is optionally buffered to a pH of about 3 to about 9.

A further aspect of the present invention comprises a composition for topical administration comprising a self-emulsifying admixture.

Another aspect of the present invention comprises a kit comprising: a first composition comprising a hydrophilic composition; and a second composition comprising a hydrophobic composition. In some embodiments, the hydrophobic composition comprises an active pharmaceutical ingredient.

An additional aspect of the present invention comprises a method of increasing the release of nitric oxide from a hydrophobic composition containing a diazeniumdiolate modified macromolecule comprising: admixing a hydrophobic composition with a hydrophilic composition having a pH of about 4 to about 8 to form an admixture; and applying the admixture to the skin of a subject.

Another aspect of the present invention comprises a method of stably storing a diazeniumdiolate modified macromolecule in a hydrophobic composition and releasing nitric oxide from the diazeniumdiolate modified macromolecule. Some embodiments include admixing the hydrophobic composition with a hydrophilic composition to form an admixture, wherein the hydrophobic composition comprises the diazeniumdiolate modified macromolecule and the hydrophilic composition has a pH of about 4 to about 8.

A further aspect of the present invention comprises a method of providing a topical antimicrobial composition comprising: admixing a hydrophobic composition with a hydrophilic composition having a pH of about 4 to about 8 to form an admixture; and applying the admixture to the skin of a subject.

Another aspect of the present invention comprises a method of increasing the rate of healing for a wound comprising: topically applying an admixture having a pH of about 4 to about 8.

The foregoing and other aspects of the present invention will now be described in more detail including other embodiments described herein.

DETAILED DESCRIPTION

Figure 1:
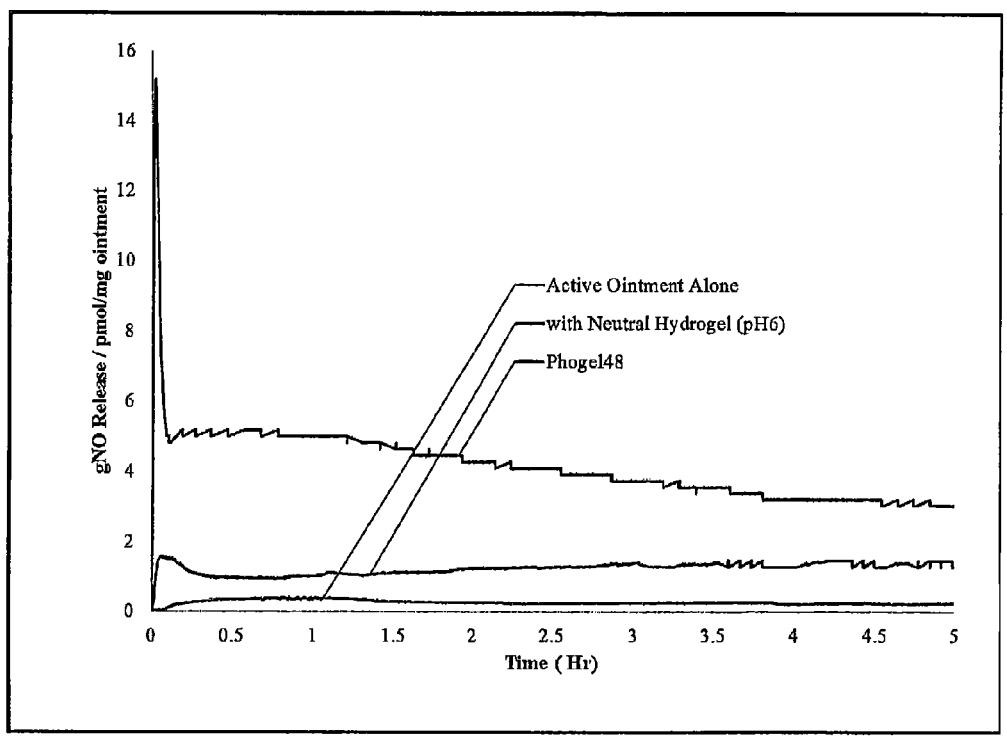
FIG. 1 shows a graph of the NO release from different formulations containing Nitricil™ NVN4 ointment (1.8% w/w NO).

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, +0.5%, or even ±0.1% of X. A range provided herein for a measureable value may include any other range and/or individual value therein.

According to some embodiments of the present invention, provided herein are topical compositions. In some embodiments, a topical composition of the present invention comprises an admixture. "Admixture" as used herein refers to a combination of at least two different compositions. In some embodiments, the at least two different compositions may be miscible. In particular embodiments, the term admixture refers to the at least two different compositions being maintained substantially isolated from one another until the proximate time of use or application. In certain embodiments, the term admixture refers to the at least two different compositions being maintained substantially isolated from one another until dispensing, such as with pharmacist dispensed products. In some embodiments, one or more compositions present in an admixture may be maintained substantially isolated from one or more other compositions present in an admixture. The term admixture is not intended to refer to a composition that is created at the time of manufacture of the composition or product, such as by the combining of ingredients to create the composition. The combining of two or more different compositions, such as 2, 3, 4, 5, 6, 7, or more compositions, to form an admixture may be achieved by mixing, blending, contacting, applying to a same area or region, emulsifying, and the like the two or more different compositions. The combining of two or more different compositions may be carried out to induce a chemical reaction. A composition may be different than another composition in the amount or concentration of one or more components, the type (e.g., chemical composition) of one or more components, and/or the presence and/or absence of one or more components.

An admixture of the present invention may comprise at least one composition that modulates a property of another composition and/or a component present in the admixture. The property modulated may be compared to the property of the composition and/or component in the absence of the admixture. For example, the admixture may comprise at least one composition (i.e., a first composition) that modulates the pH of another composition (i.e., a second composition) and/or the release of an active pharmaceutical ingredient (API) in another composition (i.e., a second composition). As used herein, release of the API refers to release of the API itself and/or release of one or more active agents from the API (e.g., where a pro-drug is the API and the active form of the drug may be released). For example, in embodiments where the API is a nitric oxide-releasing API, references to API release may refer to release of nitric oxide from the API. The pH of the admixture may be compared to the pH of the second composition when it is not in admixture with the first composition. The release of the API from the admixture may be compared to the release of the API in the absence of the admixture (i.e., the release of the individual API component and/or the release of the API from the second composition when the second composition is not in admixture with the first composition).

"Modulate," "modulating," "modulation," and grammatical variations thereof as used herein refer to an increase or reduction in a property (e.g., the pH and/or release of an API) in an admixture of the present invention compared to the property in the absence of the admixture. As used herein, the terms "increase," "increases," "increased," "increasing" and similar terms indicate an elevation in a property (e.g., the pH and/or release of an API) of at least about 5%, 10%, 25%, 50%, 75%, 100%, 150%, 200%, 300%, 400%, 500% or more compared to the property in the absence of the admixture. As used herein, the terms "reduce," "reduces," "reduced," "reduction" and similar terms refer to a decrease in a property (e.g., the pH and/or release of an API) of at least about 5%, 10%, 25%, 35%, 50%, 75%, 80%, 85%, 90%, 95%, 97% or more compared to the property in the absence of the admixture.

In some embodiments, an admixture may comprise at least two compositions (i.e., a first composition and a second composition). The first composition may modulate the pH of the second composition and/or the release of an API present in the second composition or vice versa. Admixtures comprising two compositions are described herein for purposes of illustration, but it is understood that the admixture may comprise more than two different compositions, such as, but not limited to, 2, 3, 4, 5, 6, 7, or more compositions. One or more of the compositions present in the admixture may modulate a property of another composition in the admixture. The property modulated may be the same property or a different property. In some embodiments, two or more different compositions in an admixture may together modulate a property of another composition in the admixture.

An admixture of the present invention may be formed by direct and/or indirect exposure of at least one component in a first composition to at least one component in a second composition. For example, an admixture may be formed by mixing and/or combining the first composition and second composition prior to, during, and/or after topical application to a subject. The admixture may comprise a single phase even though it may be prepared from at least two different compositions. A further example of direct exposure of a first composition and second composition to form an admixture may occur by applying one or more layers of the second composition onto a subject and then applying one or more layers of the first composition onto a subject or vice versa. Indirect exposure may occur by applying a second composition onto a subject and then applying a first composition onto a subject through a substrate, such as, but not limited to, a cloth, bandage, gauze, and the like, or vice versa to form an admixture.

In certain embodiments, the admixture may be self-emulsifying. In particular embodiments, the self-emulsifying admixture comprises a first composition comprising water and a second composition comprising an oil, amphiphilic agent and/or emulsifying agent. Example emulsifying agents include, but are not limited to, phosphatidyl cholines; lecithin; surfactants such as polyethoxylated compounds including Tween 80 polysorbate 20, 21, 40, 60, 61, 65, 81, 85, 120 and other polyoxyethylene adducts of sorbitan esters, fatty acids, fatty alcohols, lanolin, lanolin alcohols, castor oil (natural or hydrogenated), or alkylbenzenes; and any combination thereof.

A self-emulsifying admixture may form a spontaneous emulsion (e.g., with the application of minimal or no mechanical energy) upon combining the at least two compositions of the admixture. In some embodiments, the self-emulsifying admixture may not require and/or need heat in order to form a spontaneous emulsion. In some embodiments, a self-emulsifying admixture may emulsify spontaneously via a chemical reaction under minimal or no mechanical and/or external force to form a spontaneous emulsion. For example, the self-emulsifying admixture may be formed by a subject and/or third party by mixing the at least two compositions of the admixture with their hands. In some embodiments, the minimal mechanical force may provide sufficient shear to emulsify the at least two compositions of the admixture. In some embodiments, the minimal mechanical force to emulsify the at least two compositions of the admixture may have a shear rate in a range of about $1 \text{ s}^{-1}$ to about $5,000 \text{ s}^{-1}$, such as, for example, about $10 \text{ s}^{-1}$ to about $200 \text{ s}^{-1}$, about $100 \text{ s}^{-1}$ to about $1000 \text{ s}^{-1}$, about $500 \text{ s}^{-1}$ to about $3000 \text{ s}^{-1}$, or about $10 \text{ s}^{-1}$ to about $2500 \text{ s}^{-1}$.

Figure 11:
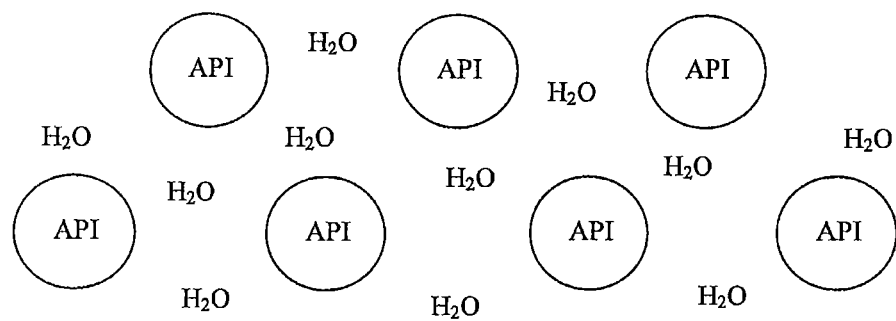
FIG. 11 illustrates an example schematic of oil droplets encompassing an API with water surrounding the oil droplets.

The self-emulsifying admixture upon forming an emulsion may contain and/or be a single phase. In some embodiments, the self-emulsifying admixture may be a coarse emulsion, a microemulsion or a nanoemulsion. In some embodiments, the self-emulsifying admixture may be a non-separating or continuous emulsion and/or a homogeneous composition. In some embodiments, a self-emulsifying admixture may encapsulate a hydrophobic component in a hydrophilic component. As illustrated in FIG. 11, in some embodiments, a self-emulsifying admixture may contain droplets of an oil or a hydrophobic phase with water or a hydrophilic phase surrounding the droplets, and the droplets may encapsulate an API.

In some embodiments, a self-emulsifying admixture may be formed upon combining a hydrophobic composition and a hydrophilic composition. Some embodiments include that the hydrophobic composition comprises at least one hydrophobic base (e.g., 1, 2, 3, 4, or more hydrophobic bases), an amphiphilic compound, and/or a cosolvent and that the hydrophilic composition comprises water, a humectant, and/or a polymer. In some embodiments, the hydrophilic composition may be a hydrogel. In some embodiments, the hydrophobic composition may comprise an API, such as, for example, a NO-releasing API. In some embodiments, the hydrophobic composition may be determinative as to whether the composition is a self-emulsifying composition. In some embodiments, the hydrophobic composition may not comprise a component with a hydrophilic property, such as, for example, a strongly hydrophilic polyethylene glycol (e.g., PEG 400). In some embodiments, the hydrophobic composition does not comprise a component with a hydrophilic-lipophilic balance (HLB) value greater than 15.

In some embodiments, the admixture is a continuous emulsion (i.e., a non-separating emulsion). In some embodiments, the admixture may remain as a continuous emulsion and/or may stay together as a single phase for at least 1, 2, 3, 4, 5, 6, or more days, or 1, 2, 3, 4, 5, 6, or more weeks, or 1, 2, 3, 4, 5, 6, or more months. In some embodiments, the admixture may be a continuous emulsion for a period of time sufficient to apply the composition to a subject. A composition that separates out into two or more phases within 1 day of combination of two or more parts of the composition is not considered to be a self-emulsifying admixture and/or a continuous emulsion.

In some embodiments, a self-emulsifying admixture may have a droplet size (e.g., diameter) of greater than 100 µm. In some embodiments, the self-emulsifying admixture may form or produce an emulsion that may have a droplet size of about 100 µm or less, such as, but not limited to, about 90 µm, 70 µm, 50 µm, 30 µm or less, or any range and/or individual value therein. In some embodiments, the self-emulsifying admixture may form or produce an emulsion that may have a droplet size of greater than 1 µm. In some embodiments self-emulsifying admixture may form or produce a nanoemulsion that may have a droplet size of about 400 nm or less, such as, but not limited to, about 300 nm, 200 nm, 100 nm, 50 nm or less, or any range and/or individual value therein. In some embodiments, a self-emulsifying admixture may comprise droplets that are substantially uniform in size.

The first composition in the admixture may be configured to modulate the release of an API present in the second composition such as, but not limited to, an NO releasing API. In some embodiments, when an admixture is formed comprising the first and second compositions, water present in the first composition may contact the second composition to modulate the release of an API present in the second composition, such as, but not limited to, an NO releasing API. Alternatively or in addition, in some embodiments, the first composition in an admixture may modulate the pH of the second composition in the admixture, thereby modulating the release of an API present in the second composition, such as, but not limited to, an NO releasing API. In some embodiments, the first composition in an admixture may be configured to supply water to the second composition in the admixture and/or configured to modulate the pH of the second composition in the admixture. In some embodiments, an admixture of the present invention may increase the solubility of an API (e.g., an NO-releasing API) and/or may increase the bioavailability of an API or an active component of an API (e.g., NO).

The inventors of the present invention surprisingly discovered that an admixture comprising an emulsion of water (i.e., a hydrophilic phase) and oil (i.e., a hydrophobic phase) could be prepared that provided sufficient NO release. It was further surprisingly discovered by the inventors that an admixture having a single phase could be prepared upon combination of a hydrophobic composition and hydrophilic composition, and that such composition could provide sufficient NO release. Self-emulsifying admixtures as described herein were also surprisingly discovered by the inventors.

An admixture of the present invention may provide a particular release pattern for an API present in the admixture. The API release pattern may be determined by comparing the amount or concentration of API released over a period of time and/or the rate of release of an API from the admixture over a period of time. In some embodiments, the at least two different compositions present in the admixture are selected to provide a particular API release pattern. The API release pattern may be desirable for a particular injury, disease, disorder, or treatment indication. In some embodiments, the admixture may be configured to provide a particular release pattern of an API present in the admixture.

In some embodiments, the at least two different compositions present in the admixture may be selected to provide the admixture with a pH of less than about pH 11, such as, but not limited to, about 11, 10, 9, 8, 7, 6, 5, 4, 3, or less. In some embodiments, the at least two different compositions present in the admixture may be selected to provide the admixture with a pH of greater than about pH 4, such as, but not limited to, about 4, 5, 6, 7, 8, 9, 10, 11, or more. In certain embodiments, the admixture pH may be between about pH 4 to about pH 11, such as, but not limited to, about pH 4 to about pH 9, about pH 7 to about pH 9, about pH 4 to about pH 8, pH 7 to about pH 10, or about pH 5 to about pH 7. In some embodiments, at least one of the compositions present in the admixture may maintain the pH of the admixture in a particular pH range. The pH of the admixture may vary over time and this may cause the release rate of the API from the admixture to vary over time. For admixtures where the pH changes over time, the pH of the admixture may be measured within about 30 minutes after combination, in some embodiments, within about 10 minutes after combination, and in some embodiments, 2 minutes after combination. In some embodiments the pH of the admixture may be measured at about 5 minutes, 30 minutes, 1 hour, and/or 24 hours after combination.

An admixture of the present invention may provide for immediate release of the API from the admixture and/or sustained release of the API from the admixture. As used herein, immediate release refers to the release of 50% or more of the API within 4 hours of mixing and sustained release refers to the release of less than 50% of the API within 4 hours of mixing. In some embodiments, an admixture of the present invention may increase the amount of API released and/or the potency of an API present in at least one composition in the admixture by maintaining the pH of the admixture in a particular pH range compared to the release and/or potency of the API in the composition in the absence of the admixture. In certain embodiments the pH of the admixture is maintained below pH 9.

The API present in the admixture may be released substantially continuously from the admixture over a period of time. "Substantially continuously," and grammatical variants thereof as used herein refer to a release of an API from the admixture for all or part of the time such that on average the release of the API confers an overall beneficial effect on the subject. Thus, there may be one or more short, intermittent and/or regular time periods in which the API is not being released, but the overall beneficial effect of the API on the subject remains. In some embodiments, the admixture may provide an API release pattern that is substantially continuous over a period of time and provide a therapeutically effective amount of the API over the period of time. In some embodiments, the amount of API released and/or the API release rate may vary over a period of time. In certain embodiments, the admixture may comprise two or more (e.g., 2, 3, 4, 5 or more) release rates for the API.

The admixture may provide an API release pattern that is substantially constant over a period of time. "Substantially constant" as used herein refers to a measureable value, such as the amount of API or the API release rate, on average, varying less than about 20%, 15%, 10%, 5%, 1% or less over a period of time. In some embodiments, the API release rate may be substantially constant for a period of time and vary over another consecutive or nonconsecutive period of time and vice versa.

In some embodiments, the admixture may provide an API release pattern having a rapid release portion and a substantially constant release portion. The rapid release portion may comprise the amount of API released from administration (i.e., t=0) to 2 hours after administration or any range therein, such as, but not limited to, 0 to 1 hour or 0 to 30 minutes after administration. The substantially constant release portion may comprise the amount of API released from immediately after the rapid release portion to the final amount of API is released. An API may be released from an admixture of the present invention for any period of time. In some embodiments, an API may be released from the admixture for at least about 4 hours, 6 hours, 12 hours, 24 hours, 2 days, 3, days, 4 days, 5, days, 6 days, 7 days, or more, or any range and/or individual value therein. The API released from the admixture may be released in an amount that overall provides a beneficial effect on the subject and/or provides a therapeutically effective amount of the API over the period of time.

In some embodiments, a greater amount or concentration of the API may be released during the rapid release portion compared to the substantially constant release portion or vice versa. In some embodiments, the amount of API released from the admixture during the rapid release portion may be about 10%, 20%, 30%, 40%, 50%, 60%, 70%, 80%, 90%, 100%, 150%, 200%, 300%, 400%, 500%, or more, or any range and/or individual value therein, than the amount of API released during the substantially constant release portion. In other embodiments, the amount of API released from the admixture during the substantially constant release portion may be about 10%, 20%, 30%, 40%, 50%, 60%, 70%, 80%, 90%, 100%, 150%, 200%, 300%, 400%, 500%, or more, or any range and/or individual value therein, than the amount of API released during the rapid release portion.

In particular embodiments, a first composition in an admixture may modulate the pH of a second composition in the admixture such that when the admixture is formed and/or applied to the skin of a subject, the pH of the admixture is less than about 9, in further embodiments, less than about 8.5, in still further embodiments, less than about 7, and in yet further embodiments, between about 5 and about 8. In some embodiments, a first composition in an admixture may be configured to maintain and/or stabilize the pH of the admixture in a desired pH range, such as, but not limited to, a pH range of about 3 to about 11, about 3 to about 9, about 4 to about 7, about 4 to about 6, or about 5 to about 8.

An admixture of the present invention may be suitable for topical administration. The admixture may comprise a single phase even though it may be prepared or formed from two or more different compositions. The admixture may be buffered. In some embodiments, the admixture may comprise a hydrophobic composition and a hydrophilic composition. In certain embodiments, a hydrophobic composition and/or a hydrophilic composition may be a single agent or compound (i.e., component). In other embodiments, a hydrophobic composition and/or a hydrophilic composition may comprise a composition having two or more agents or compounds. In some embodiments, an admixture may comprise a hydrogel and an ointment. The hydrogel and ointment may form an admixture having a single phase that is optionally buffered. In some embodiments, the admixture comprises a hydrogel and an ointment, and the admixture may be in the form of a cream. In some embodiments, the admixture may be a self-emulsifying admixture and may comprise a hydrogel and an ointment.

In certain embodiments, an admixture of the present invention comprises a hydrophilic composition. The hydrophilic composition comprises at least one hydrophilic component. The hydrophilic composition may be a solution, suspension, lotion, gel, cream, hydrogel, and the like. In some embodiments, the hydrophilic composition is in the form of a hydrogel. "Hydrogel," as used herein, refers to a hydrophilic gel comprising a gel matrix and water. Water may be present in a hydrophilic composition in an amount of about 50% to about 99% by weight of the hydrophilic composition, or any range and/or individual value therein, such as, but not limited to, about 55% to about 95%, about 65% to about 95%, about 70% to about 99%, about 75% to about 95%, about 80% to about 90%, or about 80% to about 85% by weight of the hydrophilic composition.

The hydrophilic composition may comprise means for maintaining and/or stabilizing the pH of an admixture of the present invention. The means for maintaining and/or stabilizing the pH of an admixture may be configured to control the pH of the admixture within a desired pH range. Example means for maintaining and/or stabilizing the pH of an admixture include, but are not limited to, buffers. Examples of buffers that may be used in a hydrophilic composition include, but are not limited to, acetic acid/acetate buffers; hydrochloric acid/citrate buffers; citro-phosphate buffers; phosphate buffers; citric acid/citrate buffers; lactic acid buffers; tartaric acid buffers; malic acid buffers; glycine/HCl buffers; saline buffers such as phosphate buffered saline (PBS), Tris-buffered saline (TBS), Tris-HCl, NaCl, Tween buffered saline (TNT), phosphate buffered saline, Triton X-100 (PBT) and mixtures thereof; cacodylate buffers; barbital buffers; tris buffers; and any combination thereof.

A buffer may be present in the hydrophilic composition at a concentration of about 5 mmol to about 2 moles or any range and/or individual value therein, such as, but not limited to about 10 mmol to about 1 mole, about 100 mmol to about 750 mmol, or about 200 mmol to about 500 mmol. In some embodiments, a buffer may be present in the hydrophilic composition in an amount of about 0.1% to about 20% by weight of the hydrophilic composition or any range and/or individual value therein, such as, but not limited to, about 0.1% to about 10%, about 1% to about 15%, about 10% to about 20%, about 5% to about 15%, or about 1% to about 5% by weight of the hydrophilic composition.

In some embodiments, the hydrophilic composition may comprise a phosphate buffer. Example phosphate buffers may include at least one phosphate salt such as, but not limited to, sodium phosphate (e.g., sodium dihydrogen phosphate, disodium hydrogen phosphate, trisodium phosphate and sodium aluminum phosphate), potassium phosphate (e.g., potassium phosphate monobasic and potassium phosphate dibasic), rubidium phosphate, caesium phosphate, and ammonium phosphate, and/or at least one phosphoric acid such as, but not limited to, pyrophosphoric acid, triphosphoric acid, and orthophosphoric acid. The hydrophilic composition may have a total phosphate concentration of about 5 mmol to about 1 mole of phosphate or any range and/or individual value therein, such as, but not limited to, about 10 mmol to about 750 mmol, about 150 mmol to about 500 mmol, or about 200 mmol to about 400 mmol. In certain embodiments, the hydrophilic composition may have a phosphate buffer present in an amount of about 1% to about 20% by weight of the hydrophilic composition, such as, but not limited to about 1% to about 15% by weight, about 5% to about 15% by weight, about 10% to about 20%, about 5% to about 10% by weight, about 1% to about 5%, or about 4% to about 8% by weight of the hydrophilic composition.

In certain embodiments, a hydrophilic composition may comprise a buffering agent. Example buffering agents include, but are not limited to, citric acid, acetic acid, lactic acid, boric acid, succinic acid, malic acid, sodium hydroxide, potassium hydroxide, and any combination thereof. A buffering agent may be present in a hydrophilic composition of the present invention in an amount of about 0.01% to about 5% by weight of the hydrophilic composition or any range and/or individual value therein, such as, but not limited to, about 0.05% to about 3%, about 1% to about 4%, or about 1.5% to about 3.5% by weight of the hydrophilic composition.

In some embodiments, the hydrophilic composition does not comprise or is substantially devoid of a buffer and/or a buffering agent. In some embodiments, the hydrophilic composition is unbuffered (i.e., the pH of the hydrophilic composition is not stabilized with a buffer and/or a buffering agent).

Thus, in certain embodiments, an admixture of the present invention may comprise a hydrophilic composition such as, but not limited to, a hydrogel, that is optionally buffered. The hydrophilic composition may be pH dependent. The hydrophilic composition may be configured to have a buffer capacity of at least about 4 to about 8, or any range and/or individual value therein, such as, but not limited to, about 4 to about 7, about 5 to about 6, about 5 to about 8, or about 6 to about 8. The hydrophilic composition may be configured to maintain and/or stabilize the pH of an admixture within about 0.5 or more pH units such as, for example, about 1, 2, or 3 pH units, of the pH of the hydrophilic composition. The pH of the admixture may be maintained and/or stabilized when the admixture is formed and/or at the site of application (e.g., the skin of a subject and/or a wound bed) for the admixture. For example, when an admixture comprising a hydrophilic composition having a pH of about 5 is formed with an additional composition and applied to the skin of a subject, the hydrophilic composition may be configured to maintain and/or stabilize the pH of the admixture within about 0.5 pH units of the hydrophilic composition pH (i.e., the hydrophilic composition may maintain the pH of the admixture in a pH range of about 4.5 to 5.5). In some embodiments, a hydrophilic composition may be configured to maintain and/or stabilize the pH of an admixture in a pH range of about pH 3 to about pH 6, about pH 3 to about pH 5, about pH 3 to about pH 4, about pH 4 to about pH 8, about pH 4 to about pH 7, about pH 4 to about pH 6, about pH 5 to about pH 7, about pH 5 to about pH 6, about pH 6 to about pH 7, or any other range therein. The admixture may thus provide a particular pH to the site of application (e.g., wound bed), which may increase or decrease the pH of the site of application in the absence of the admixture.

A hydrophilic composition of the present invention may have any suitable pH, such as a pH of about 1 or more (e.g., about 2, 3, 4, 5, 6, 7, 8, 9, 10, 11, 12, 13, or 14). In some embodiments, the hydrophilic composition may be configured to have a pH in a range of about 3 to about 8 or any range and/or individual value therein, such as about 3 to about 4 or about 4 to about 6. In certain embodiments, the hydrophilic composition may be configured to have a pH of about 5. In some embodiments, the hydrophilic composition may be buffered.

A hydrophilic composition may comprise a natural and/or synthetic polymer. Example polymers include, but are not limited to, polysaccharides such as chitosan and chitin; charged celluloses and pharmaceutically acceptable salts thereof; acrylic acids such as polyacrylic polymers such as polyacrylic acid, polyacrylate polymers, cross-linked polyacrylate polymers, cross-linked polyacrylic acids, polyacrylic acid polymers commercially available from Lubrizol of Wickliffe, Ohio under the trademark CARBOPOL®, and mixtures thereof; and any combination thereof. In some embodiments, a hydrophilic composition comprises a charged cellulose or a pharmaceutically acceptable salt thereof. Example charged celluloses or pharmaceutically acceptable salts thereof include, but are not limited to, ionic celluloses, carboxymethyl cellulose and salts thereof, hydroxyethyl carboxymethyl cellulose, hydroxypropyl carboxymethyl cellulose, sulfoethyl cellulose, hydroxyethyl sulfoethyl cellulose, hydroxypropyl sulfoethyl cellulose, hydroxyethyl cellulose ethoxylate, hydroxypropylmethyl cellulose, methyl cellulose, ethyl cellulose, hydroxyethyl cellulose, hydroxyethylmethyl cellulose, carrageenan, chitosan, xanthan gum, sodium alginate, propylene glycol aginate, alginic acid and its salts, and any combination thereof. In some embodiments, a hydrophilic composition may comprise carboxymethyl cellulose and/or a salt thereof. In some embodiments, a hydrophilic composition may comprise hydroxyethyl cellulose ethoxylate, quaternized. In some embodiments, a hydrophilic composition may comprise chitosan.

A polymer, such as, but not limited to, charged cellulose or a pharmaceutically acceptable salt thereof, may be present in a hydrophilic composition in an amount of about 0.1% to about 15% by weight of the hydrophilic composition or any range and/or individual value therein, such as, but not limited to, about 0.3% to about 10%, about 0.5% to about 10%, about 1% to about 10% or about 1% to about 5% by weight of the hydrophilic composition. In certain embodiments, a polymer, such as, but not limited to, charged cellulose and/or a pharmaceutically acceptable salt thereof (e.g., carboxymethyl cellulose and salts thereof), may be present in a hydrophilic composition in an amount of about 0.1%, 0.3%, 0.5%, 1%, 2%, 3%, 4%, 5%, 6%, 7%, 8%, 9%, 10%, 11%, 12%, 13%, 14%, or 15% by weight of the hydrophilic composition or any range and/or individual value therein.

A hydrophilic composition may comprise a polyhydric alcohol. Example polyhydric alcohols include, but are not limited to, glycerol, glycols, propylene glycol, hexylene glycol, polyethylene glycol, polypropylene glycol, triethylene glycol, neopental glycols, triethanolamine, diethanolamine, ethanolamione, butylene glycol, polyethylene glycol, n-methyl diethanolamine, isopropanolamine, sorbitol, arabitol, erythritol, HSH, isomalt, lactitol maltitol, mannitol, xylitol, threitol, ribitol, galactitol, fucitol, iditol, inositol, volemitol, and any combination thereof. In some embodiments, a hydrophilic composition may comprise glycerol. In some embodiments, a hydrophilic composition may comprise a glycol, such as hexylene glycol.

A polyhydric alcohol may be present in a hydrophilic composition in an amount of about 1% to about 30% by weight of the hydrophilic composition or any range and/or individual value therein, such as, but not limited to, about 1% to about 25%, about 5% to about 15%, about 5% to about 20%, about 10% to about 30%, or about 15% to about 25% by weight of the hydrophilic composition. In certain embodiments, a polyhydric alcohol may be present in a hydrophilic composition in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the hydrophilic composition or any range and/or individual value therein.

A hydrophilic composition may comprise a preservative. A preservative may be present in a hydrophilic composition in an amount of about 0.01% to about 2% by weight of the composition or any range and/or individual value therein, such as, but not limited to, about 0.05% to about 1%, about 0.05% to about 0.5%, or about 0.1% to about 1% by weight of the hydrophilic composition. In certain embodiments, a preservative is present in a hydrophilic composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the hydrophilic composition or any range and/or individual value therein.

Example preservatives that may be present in a hydrophilic composition of the present invention include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A hydrophilic composition may comprise a neutralizing agent. A neutralizing agent may be present in a hydrophilic composition in an amount sufficient to provide the hydrophilic composition with a pH of about 3 to about 8, or any range and/or individual value therein, such as, but not limited to, about 4 to about 7 or about 6 to about 7. In some embodiments, a neutralizing agent adjusts the pH of the hydrophilic composition. In certain embodiments of the present invention, a neutralizing agent may be present in a hydrophilic composition of the present invention in an amount sufficient for the hydrophilic composition to have a pH of about 3, 3.5, 4, 4.5, 5, 5.5, 6, 6.5, 7, 7.5, or 8 or any range and/or individual value therein. Example neutralizing agents that may be present in a hydrophilic composition include, but are not limited to, bases such as sodium hydroxide, potassium hydroxide, and mixtures thereof; acids such as hydrochloric acid, citric acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof.

According to some embodiments, a hydrophilic composition may be antimicrobial. A hydrophilic composition may be cosmetically elegant. "Cosmetically elegant" as used herein, refers to a composition that is attractive for application to the skin, which may include mucosa. In some embodiments, a composition may be cosmetically elegant for the skin and/or mucosa. A cosmetically elegant composition of the present invention may have one or more of the following properties: suitable consistency or viscosity for topical application (e.g., easy to spread onto the skin and does not run), suitable texture for topical application (e.g., a smooth or soft composition that is not gritty), ability to absorb and/or permeate the skin, non-sticky or not tacky, does not leave a residue, leaves the skin feeling good, and after application does not leave the skin oily or dry. In some embodiments, a hydrophilic composition may have a viscosity of about 5,000 cP (centipoise) to about 100,000 cP, or any range and/or individual value therein, such as, but not limited to, about 10,000 cP to about 50,000 cP, about 20,000 cP to about 40,000 cP, about 30,000 cP to about 50,000 cP, about 50,000 cP to about 100,000 cP, or about 30,000 cP to about 75,000 cP.

A hydrophilic composition such as, but not limited to, a hydrogel, of the present invention may be suitable in an admixture of the present invention with one or more, such as, but not limited to, 2, 3, 4, or more, different compositions. A hydrophilic composition, such as, but not limited to, a hydrogel, of the present invention may be used as a drug delivery system and/or a drug release system when in an admixture of the present invention. For example, a hydrophilic composition may be configured to modulate the release of an active pharmaceutical ingredient (API) in a second composition when an admixture comprising the hydrophilic composition and second composition is formed and/or administered. Alternatively or in addition, a hydrophilic composition may be configured to modulate the pH of a second composition when an admixture comprising the hydrophilic composition and second composition is formed and/or administered. In some embodiments, a hydrophilic composition may be configured to modulate the pH of a second composition comprising a nitric oxide (NO) releasing API and/or the rate of NO release from a NO releasing API when an admixture comprising the hydrophilic composition and second composition is formed and/or administered. In certain embodiments, the second composition may be a hydrophobic composition, such as, but not limited to, an ointment. In some embodiments, a hydrophilic composition may be configured to modulate the pH of an admixture in which it is present within a desired pH range.

An admixture of the present invention may have any suitable pH. In some embodiments, the admixture may have a pH of about 1, 2, 3, 4, 5, 6, 7, 8, 9, 10, 11, 12, 13, or 14. In some embodiments, the admixture may be configured to have a pH in a range of about pH 2 to about pH 9, such as about pH 4 to about pH 9, about pH 3 to about pH 6, about pH 3 to about pH 5, about pH 3 to about pH 4, about pH 4 to about pH 8, about pH 4 to about pH 7, about pH 4 to about pH 6, about pH 5 to about pH 7, about pH 5 to about pH 6, about pH 6 to about pH 7, about pH 4 to about pH 8, or about pH 5 to about pH 8, or any other range therein. In certain embodiments, an admixture of the present invention is buffered to a suitable pH. In some embodiments, an admixture of the present invention is unbuffered and/or the admixture does not comprise or is substantially devoid of a buffer and/or a buffering agent.

In some embodiments, an admixture of the present invention may comprise an active pharmaceutical ingredient (API). Any suitable API or combinations of APIs may be included in an admixture of the present invention. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents, and any combination thereof. Example APIs include, but are not limited to, those described in International Application No. PCT/US2013/028223, which is incorporated herein by reference in its entirety. In some embodiments, the admixture and/or, API does not comprise acidified nitrite. "Acidified nitrite", as used herein, refers to a nitric oxide releasing composition where the primary mechanism of nitric oxide release is when a nitrite is reduced, in the presence of an acid, to dinitrogen trioxide, which can dissociate into nitric oxide and nitrous oxide.

Examples of antimicrobial agents include, but are not limited to, penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic anti-bacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, Linezolid, Synercid, Aztreonam, and Metronidazole, Epiroprim, Sanfetrinem sodium, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil.

Examples of topical anti-acne agents include, but are not limited to, adapalene, azelaic acid, benzoyl peroxide, clindamycin and clindamycin phosphate, doxycycline, erythromycin, keratolytics such as salicylic acid and retinoic acid (Retin-A"), norgestimate, organic peroxides, retinoids such as isotretinoin and tretinoin, sulfacetamide sodium, and tazarotene. Particular anti-acne agents include adapalene, azelaic acid, benzoyl peroxide, clindamycin (e.g., clindamycin phosphate), doxycycline (e.g., doxycycline hyclate), erythromycin, isotretinoin, norgestimate, sulfacetamide sodium, tazarotene, etretinate and acetretin.

Examples of antihistamine agents include, but are not limited to, diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include, but are not limited to, alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include, but are not limited to, nonsteroidal anti-inflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include, but are not limited to, alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include, but are not limited to, alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocaine; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include, but are not limited to, thrombin, phytonadione, protamine sulfate, aminocaproic acid, tranexamic acid, carbazochrome, carbaxochrome sodium sulfanate, rutin and hesperidin.

An API may be present in any one of the compositions used to form an admixture of the present invention. In certain embodiments, at least one composition used to form an admixture comprises a nitric oxide (NO)-releasing API. In some embodiments, at least composition used to form an admixture does not contain an API, such as, but not limited to, a NO-releasing API. In some embodiments, a composition used to form an admixture may comprise at least one API, but the composition does not comprise a NO-releasing API. In certain embodiments, an admixture comprises a hydrophilic composition and the hydrophilic composition does not comprise a NO-releasing API. In some embodiments, an admixture of the present invention does not comprise an active pharmaceutical ingredient (API).

In certain embodiments, an admixture of the present invention may comprise at least one API, such as, but not limited to, a nitric oxide-releasing active pharmaceutical ingredient. In some embodiments, an admixture of the present invention comprises a nitric oxide-releasing active pharmaceutical ingredient in an amount of about 0.01% to about 5% w/w of nitric oxide or any range and/or individual value therein, such as about 0.1% to about 3%, about 0.1% to about 1.5%, or about 1% to about 5% w/w of nitric oxide.

"Nitric oxide releasing active pharmaceutical ingredient" and "NO releasing API," as used herein, refer to a compound or other composition that provides nitric oxide to the skin of a subject, but is not gaseous nitric oxide. In some embodiments, the NO releasing API includes a nitric oxide-releasing compound, hereinafter referred to as a "NO-releasing compound." A NO-releasing compound includes at least one NO donor, which is a functional group that may release nitric oxide under certain conditions. In some embodiments, the at least one NO donor of a NO-releasing compound releases NO when in contact with a composition of the present invention. In certain embodiments, a composition of the present invention modulates the amount of NO released from a NO-releasing compound and/or the rate of NO released from a NO-releasing compound. In some embodiments, a composition of the present invention increases the amount of NO released from a NO-releasing compound and/or the rate of NO released from a NO-releasing compound.

Any suitable NO-releasing compound may be used. In some embodiments, the NO-releasing compound includes a small molecule compound that includes a NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes a NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 μm and may comprise the aggregation of two or more macromolecules, whereby the macromolecular structure is further modified with an NO donor group.

In some embodiments, the NO-releasing compound includes a diazeniumdiolate functional group as a NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in a second composition as described herein. Additionally, the NO donor may be incorporated into or onto the small molecule or macromolecule through covalent and/or non-covalent interactions.

A NO-releasing macromolecule may be in the form of a NO-releasing particle, such as those described in U.S. Application Publication No. 2009/0214618 and U.S. Pat. No. 8,282,967, the disclosures of which are incorporated by reference herein in their entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Publication No. WO/2013/029009; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Publication No. WO/2012/100174, the disclosure of which is incorporated herein by reference in its entirety.

In some embodiments, an admixture of the present invention may increase the amount of NO released from the admixture compared to the amount of NO released from at least one composition used to form the admixture over the same period of time. For example, when an admixture comprising a hydrophilic composition and a hydrophobic composition such as, but not limited to, an ointment as described herein, is formed, the amount of NO released from the admixture may be increased compared to the amount of NO released from the hydrophobic composition alone (i.e., in the absence of the hydrophilic composition or admixture). In certain embodiments, an admixture of the present invention may increase the amount of NO released by at least about 10%, 20%, 30%, 40%, 50%, 60%, 70%, 80%, 90, 100%, 150%, 200%, 300%, 400%, or more, or any range and/or individual value therein, compared to the amount of NO released from at least one composition used to form the admixture over the same period of time. An admixture of the present invention may release about 1.5 to about 100 times more NO than the amount of NO from at least one composition used to form the admixture over the same period of time, or any range and/or individual value therein, such as, but not limited to about 2 to about 10 times more NO or about 5 to about 50 times more NO.

According to some embodiments, an admixture comprises means for stabilizing and/or maintaining the pH of the admixture. Example means for stabilizing and/or maintaining the pH of the admixture include, but are not limited to, buffers such as those described herein. In some embodiments, the admixture may comprise a nitric oxide-releasing active pharmaceutical ingredient in an amount of about 0.01% to about 5% w/w of nitric oxide and have a pH of about 4 to about 9. An admixture of the present invention may be cosmetically elegant and/or antimicrobial. In some embodiments, an admixture of the present invention is self-emulsifying.

In some embodiments, an admixture of the present invention may comprise a hydrophilic composition as described herein and a hydrophobic composition. The hydrophobic composition may be a liquid, solution, ointment, and the like. The hydrophobic composition comprises at least one hydrophobic component, such as, but not limited to, a hydrophobic base. Example hydrophobic compositions include those described in International Application Nos. PCT/US2010/046173 and PCT/US2013/028223, which are incorporated herein by reference in their entirety. In some embodiments, the hydrophobic composition is an ointment.

In some embodiments, an admixture of the present invention may comprise a polymer, such as, but not limited to, a charged cellulose or a pharmaceutically acceptable salt thereof; a humectant, such as, but not limited to, a polyhydric alcohol; water; a hydrophobic base; an amphiphilic compound and/or a cosolvent. The admixture may be unbuffered and/or the admixture does not comprise or is substantially devoid of a buffer and/or a buffering agent. In some embodiments, the admixture may have a pH in a range of about pH 4 to about pH 8.

In certain embodiments, an admixture of the present invention may comprise a polymer, such as, but not limited to, a charged cellulose or a pharmaceutically acceptable salt thereof; a polyhydric alcohol; a hydrophobic base; an API; and optionally an amphiphilic compound or an emulsifying agent. In some embodiments, the API may comprise a NO-releasing compound. The admixture may further comprise a buffer, such as, but not limited to, a phosphate buffer, and be buffered to a pH of about 4 to about 9 or any range and/or individual value therein.

At least one hydrophobic base may be present in an admixture of the present invention. In some embodiments, a hydrophobic base may be present in a hydrophobic composition that may be used to form an admixture of the present invention. "Hydrophobic base" as used herein refers to a natural and/or synthetic fat, wax, oil, and/or the like. Any suitable hydrophobic base may be used in an admixture of the present invention. In certain embodiments, an admixture comprises two or more hydrophobic bases, such as, but not limited to, 2, 3, 4, 5, or more hydrophobic bases. In certain embodiments, a hydrophobic base in addition to having hydrophobic properties, may also have hydrophilic properties and thus may be an amphiphilic base. Example hydrophobic bases include, but are not limited to, branched and unbranched hydrocarbons, branched and unbranched hydrocarbon waxes, vaseline, hydrocarbon gel, liquid paraffin, white petrolatum, petrolatum, microcrystalline wax, andelilla wax, carnauba wax, lanolin (wool wax), wool wax alcohol, esparto grass wax, cork wax, guaruma wax, rice bran wax, sugar cane wax, berry wax, ouricury wax, soy wax, jojoba oil, uropygial grease, ceresine, paraffin waxes, micro waxes, plant oils, animal oils, carnauba wax, beeswax, cacao butter, hard fat, mineral oil, vegetable oil, avocado oil, borage oil, canola oil, castor oil, chamomile oil, coconut oil, corn oil, cottonseed oil, rapeseed oil, evening primrose oil, safflower oil, sunflower oil, soybean oil, sweet almond, palm oil, palm kernel oil, arctium lappa seed oil, sesame oil, borgo officialis seed oil, brassica campestris oleifera oil, brevoortia oil, bubulum oil, cistus ladaniferus oil, elaeis guineensis oil, almond oil, pine oil, olive oil, peanut oil, wheat germ oil, grape seed oil, thistle oil, lard, tallow, palm olein, illipe butter, shea butter, cocoa butter, kokum butter, sal butter, lecithin, japan wax lanolin, partially hydrogenated vegetable oils, hydrophobic polymers, and any combination thereof.

In some embodiments, a hydrophobic base may comprise a hydrophobic polymer. Any suitable hydrophobic polymer may be used in an admixture of the present invention. Example hydrophobic polymers include, but are not limited to hydrocarbon polymers and/or co-polymers, aromatic polyurethanes, silicone rubber, polysiloxanes, polycaprolactone, polycarbonate, polyvinylchloride, polyethylene, polyethylene glycols (6-4000), poly-L-lactide, poly-DL-glycolide, polyetheretherketone (PEEK), polyamide, polyimide and polyvinyl acetate. In certain embodiments, a hydrophobic base may be an amphiphilic base, such as, but not limited to, a polyethylene glycol (6-4000). In particular embodiments of the present invention, an admixture of the present invention comprises one or more hydrocarbon polymers and/or co-polymers. In certain embodiments, an admixture of the present invention may comprise one or more hydrocarbon polymers and/or co-polymers, such as, but not limited to, those commercially available from Calumet Specialty Products Partners of Indianapolis, Ind. under the trademark Versagel® and/or those commercially available from Croda International Plc of East Yorkshire, United Kingdom under the trade name Crodabase SQ.

In some embodiments, an admixture may comprise at least one hydrophobic base comprising one or more plant and/or mineral oils. Any suitable oil may be used in the admixtures of the present invention. Example mineral oils include, but are not limited to, light mineral oil, white mineral oil, paraffinic oils, naphtenic oils, aromatic oils, and any combination thereof.

One or more hydrophobic bases may be present in a hydrophobic composition used to form an admixture of the present invention. One or more hydrophobic bases (e.g., 1, 2, 3, 4, 5 or more hydrophobic bases), alone or together, may be present in a hydrophobic composition at a concentration from about 1% to about 99% by weight of the hydrophobic composition or any range and/or individual value therein, such as, but not limited to, from about 2% to about 20% by weight, about 1% to about 10% by weight, about 1% to about 15% by weight, about 15% to about 65% by weight, about 25% to about 98% by weight, about 30% to about 98% by weight, about 35% to about 99% by weight, about 35% to about 90% by weight, about 25% to about 50% by weight, about 25% to about 55% by weight, about 30% to about 50% by weight, about 35% to about 55% by weight, about 40% to about 80% by weight, about 50% to about 90% by weight, about 65% to about 95% by weight, about 70% to about 80% by weight, about 75% to about 95% by weight, about 80% to about 99% by weight, about 90% to about 99% by weight, or about 50% to about 70% by weight of the hydrophobic composition. In certain embodiments, one or more hydrophobic bases, alone or together, may be present in a hydrophobic composition used to form an admixture at a concentration from about 50% to about 90% by weight of the hydrophobic composition. In some embodiments, one or more hydrophobic bases, alone or together, may be present in a hydrophobic composition used to form an admixture at a concentration from about 70% to about 99% by weight of the hydrophobic composition.

"Amphiphilic compound" as used herein refers to a compound comprising hydrophilic and hydrophobic properties. An amphiphilic compound may comprise two or more compounds, each of which may provide the hydrophilic property and/or the hydrophobic property. In some embodiments, the amphiphilic compound may comprise one compound having hydrophilic and hydrophobic properties. In particular embodiments of the present invention, an amphiphilic compound may absorb moisture without substantially absorbing vaporous moisture. An amphiphilic compound may have a hydrophilic-lipophilic balance (HLB) value of 12 to 20 or any range and/or individual value therein, such as, but not limited to, 15 to 20 or 18 to 20. In certain embodiments of the present invention, an amphiphilic compound may have a HLB value of 19.

Example amphiphilic compounds include, but are not limited to, fatty acid esters. One or more fatty acid ester(s) may be present in an admixture of the present invention, such as 2, 3, 4, or more fatty acid esters. Example fatty acid esters include, but are not limited to, $C_6$-$C_{22}$ alkyl and/or alkenyl fatty acid esters such as methyl laurate, ethyl laurate, ethyl myristate, ethyl palmitate, ethyl linoleate, propyl isobutylate, isopropyl laurate, isopropyl myristate, isopropyl palmitate, oleyl myristate, oleyl stearate, and oleyl oleate; ether-esters such as fatty acid esters of ethoxylated fatty alcohols; polyhydric alcohol esters such as ethylene glycol mono- and di-fatty acid esters, diethylene glycol mono- and di-fatty acid esters; polyethylene glycol (6-2000) fatty acid mono- and/or diesters such as PEG-6-laurate, PEG-6-stearate, PEG-8-dilaurate, PEG-8-distearate, etc.; polyethylene glycol glycerol fatty acid esters such as PEG-20-glyceryl laurate, PEG-20-glyceryl stearate, and PEG-20-glyceryl oleate; propylene glycol mono- and di-fatty acid esters; polypropylene glycol 2000 monooleate; polypropylene glycol 2000 monostearate; ethoxylated propylene glycol monostearate; glyceryl mono- and di-fatty acid esters; polyglycerol fatty acid esters such as polyglyceryl-10 laurate, etc.; ethoxylated glyceryl monostearate; 1,3-butylene glycol monostearate; 1,3-butylene glycol distearate; polyoxyethylene polyol fatty acid ester; sorbitan fatty acid esters including sorbitan trioleate and sorbitan monolaurate; polyethylene glycol sorbitan fatty acid esters such as PEG-6 sorbitan monooleate; polyoxyethylene sorbitan fatty acid esters including polyoxyethylene (20) sorbitan monolaurate; sucrose fatty acid esters such as saccharose monopalmitate and saccharose monostearate; wax esters such as beeswax, spermaceti, myristyl myristate, stearyl stearate and arachidyl behenate; polyethylene glycol alkyl ethers such as PEG-10 oleyl ether or PEG-9 cetyl ether; polyethylene glycol alkyl phenols such as PEG-10-100 nonyl phenol; polyoxyethylene-polyoxypropylene block copolymers such as poloxamer 188; sterol esters such as cholesterol fatty acid esters, and any combination thereof.

In certain embodiments, a fatty acid ester may comprise a polyethylene glycol (PEG) glyceride. The polyethylene glycol portion of a PEG glyceride may provide the hydrophilic property of an amphiphilic compound and may include, but is not limited to, PEG 5-1000 or any range and/or individual value therein, and any combination thereof. The glyceride portion of a PEG glyceride may provide the hydrophobic property of an amphiphilic compound and may include, but is not limited to, a natural and/or hydrogenated oil, such as but not limited to, castor oil, hydrogenated castor oil, vitamin A, vitamin D, vitamin E, vitamin K, a plant oil (e.g., corn oil, olive oil, peanut oil, palm kernel oil, apricot kernel oil, almond oil, etc.), and any combination thereof. Example polyethylene glycol (PEG) glycerides include, but are not limited to, PEG-20 castor oil, PEG-20 hydrogenated castor oil, PEG-20 corn glycerides, PEG-20 almond glycerides; PEG-23 trioleate, PEG-40 palm kernel oil, PEG-8 caprylic/capric glycerides, PEG-6 caprylic/capric glycerides, lauroyl macrogol-32 glyceride, stearoyl macrogol glyceride, tocopheryl PEG-1000 succinate, and any combination thereof. In some embodiments, a fatty acid ester may comprise a PEG 5-30 (i.e., PEG 5, 6, 7, 8, 9, 10, etc.) and a caprylic/capric glyceride. In particular embodiments, an admixture may comprise a PEG-5-caprylic/capric glyceride, a PEG-6-caprylic/capric glyceride, a PEG-7-caprylic/capric glyceride, and/or a PEG-8-caprylic/capric glyceride. In certain embodiments, an admixture may comprise one or more fatty acid esters such as, but not limited to, those commercially available from Sasol of Hamburg, Germany under the trademark SOFTIGEN®.

An amphiphilic compound may be present in a hydrophobic composition used to form an admixture of the present invention at a concentration from about 0.5% to about 30% by weight of the hydrophobic composition or any range and/or individual value therein, such as, but not limited to, from about 0.5% to about 10% by weight, about 2% to about 20% by weight, about 1% to about 10% by weight, about 1% to about 5% by weight, or about 5% to about 15% by weight of the hydrophobic composition. In certain embodiments, an amphiphilic compound may be present in a hydrophobic composition used to form an admixture of the present invention at a concentration of about 10% by weight of the hydrophobic composition. In some embodiments, an amphiphilic compound may be present in a hydrophobic composition used to form an admixture of the present invention at a concentration of from about 0.5% to about 10% by weight of the hydrophobic composition.

An admixture of the present invention may further comprise one or more excipients. In some embodiments, one or more excipients may be present in a hydrophobic composition that may be used to form an admixture of the present invention. Excipients for use in pharmaceutical compositions are well-known in the art and examples may be found in the Handbook of Pharmaceutical Excipients (Rowe, R. C. et al., APhA Publications; 5th ed., 2005). Classes of excipients may include, but are not limited to, an emollient, a humectant, a cosolvent, a pH modifier, a water repelling agent, an anti-foaming agent, a surfactant, a solubilizer, an emulsifying agent, a wetting agent, a penetration enhancer, an antioxidant, and/or a solvent. The excipients may be present in an admixture of the present invention at any suitable concentration. In some embodiments, an excipient may be present in a hydrophobic composition used to form an admixture of the present invention at a concentration from about 1% to about 20% by weight of the hydrophobic composition or any range and/or individual value therein, such as, but not limited to, from about 1% to about 15% by weight, about 1% to about 10% by weight, or about 5% to about 10% by weight of the hydrophobic composition.

In some embodiments, an admixture may further comprise a cosolvent. A cosolvent may be present in a hydrophobic composition used to form an admixture of the present invention at a concentration from about 1% to about 30% by weight of the hydrophobic composition or any range and/or individual value therein, such as, but not limited to, from about 1% to about 15% by weight, about 1% to about 20% by weight, about 2% to about 20% by weight, about 5% to about 25% by weight, or about 5% to about 15% by weight of the hydrophobic composition. In certain embodiments of the present invention, a cosolvent may be present in a hydrophobic composition used to form an admixture of the present invention at a concentration from about 10% to about 15% by weight of the hydrophobic composition. In some embodiments, a cosolvent may be present in a hydrophobic composition used to form an admixture of the present invention at a concentration of from about 1% to about 15% by weight of the hydrophobic composition.

Example cosolvents include, but are not limited to, a fatty acid ester, propylene glycol, glycerol, polyethylene glycol, a silicone such as cyclomethicone, and any combination thereof. In some embodiments, a cosolvent may comprise a neutral oil. In certain embodiments, a cosolvent comprises a caprylic and/or capric fatty acid ester, such as a caprylic and/or capric triglyceride. Example cosolvents include, but are not limited to, those commercially available from Sasol of Hamburg, Germany under the trademark MIGLYOL®.

An admixture may comprise a humectant. Any suitable humectant or combination of humectants may be used. A humectant may be present in a hydrophobic composition used to form an admixture of the present invention at a concentration from about 1% to about 25% by weight of the hydrophobic composition or any range and/or individual value therein, such as, but not limited to, from about 1% to about 15% by weight, about 2% to about 20% by weight, about 5% to about 10% by weight, or about 5% to about 15% by weight of the hydrophobic composition. In certain embodiments, a humectant may be present in a hydrophobic composition used to form an admixture of the present invention at a concentration from about 10% to about 15% by weight of the hydrophobic composition.

Example humectants include, but are not limited to, polyhydric alcohols, such as glycols such as diethylene glycol monoethyl ether and methoxypolyethyleneglycol; glycerols such as propylene glycol, glycerol, isopropanol, ethanol, ethylene glycol, polyethylene glycol, ethoxydiglycol or mixtures thereof; sugar polyols, such as sorbitol, xylitol and maltitol; polyols such as polydextroses; dimethyl isosorbide; quillaia; urea; and any combination thereof. In particular embodiments of the present invention, a humectant comprises an alkylene glycol, such as hexylene glycol, butylene glycol, pentylene glycol, and any combination thereof.

An admixture may comprise an emulsifying agent. Any suitable emulsifying agent or combination of emulsifying agents may be used. An emulsifying agent may be present in a hydrophobic composition used to form an admixture of the present invention at a concentration from about 2% to about 97% by weight of the hydrophobic composition or any range and/or individual value therein, such as, but not limited to, from about 2% to about 20% by weight, about 5% to about 15% by weight, about 10% to about 30%, by weight, about 25% to about 99% by weight, or about 25% to about 70% by weight of the hydrophobic composition. In certain embodiments, an emulsifying agent may be present in a hydrophobic composition used to form an admixture of the present invention at a concentration from about 10% to about 50% by weight of the hydrophobic composition.

Example emulsifying agents include, but are not limited to, phosphatidyl cholines; lecithin; surfactants such as polyethoxylated compounds including tween 80 polysorbate 20, 21, 40, 60, 61, 65, 81, 85, 120 and other polyoxyethylene adducts of sorbitan esters, fatty acids, fatty alcohols, lanolin, lanolin alcohols, castor oil (natural or hydrogenated), or alkylbenzenes; fatty alcohols such as cetyl alcohol, stearyl alcohol, behenyl alcohol, myristyl alcohol, and cetostearyl alcohol; fatty acid esters such as those commercially available from Sasol of Hamburg, Germany under the trademark MIGLYOL®; and any combination thereof.

According to some embodiments, a hydrophobic composition used to form an admixture of the present invention may comprise at least one hydrophobic base in an amount of about 55% to about 99% by weight of the hydrophobic composition and an API, such as, but not limited to, a nitric oxide-releasing API. In certain embodiments, the at least one hydrophobic base may be present in the hydrophobic composition in an amount of about 70% to about 80% by weight of the hydrophobic composition. In some embodiments, an amphiphilic base may be present in the hydrophobic composition in an amount of about 15% to about 45% by weight of the hydrophobic composition. The hydrophobic composition may optionally comprise a cosolvent in an amount of about 2% to about 30% by weight of the hydrophobic composition, a humectant in an amount of about 5% to about 10% by weight of the hydrophobic composition, an emulsifying agent in an amount of about 5% to about 25% by weight of the hydrophobic composition, and/or an amphiphilic compound in an amount of about 1% to about 10% by weight of the hydrophobic composition. The hydrophobic composition may be in the form of an ointment.

In some embodiments, a hydrophobic composition used to form an admixture of the present invention may comprise one or more hydrophobic bases in an amount of about 25% to about 99% by weight of the hydrophobic composition. In certain embodiments, at least one hydrophobic base may be present in the hydrophobic composition in an amount of about 15% to about 65%, about 25% to about 55%, or about 35% to about 55% by weight of the hydrophobic composition and/or about 1% to about 15%, about 1% to about 10%, or about 1% to about 5% by weight of the hydrophobic composition. In some embodiments, the total amount of the one or more hydrophobic bases present in the hydrophobic composition may be about 65% to about 98% by weight of the hydrophobic composition. In some embodiments, an amphiphilic compound may be present in the hydrophobic composition in an amount of about 0.5% to about 10% by weight of the hydrophobic composition. The hydrophobic composition may comprise a cosolvent in an amount of about 1% to about 20% by weight of the hydrophobic composition. In some embodiments, an API, such as, but not limited to, a nitric oxide-releasing API may be present in the hydrophobic composition. The hydrophobic composition may be in the form of an ointment.

In some embodiments, a hydrophobic composition used to form an admixture of the present invention may comprise one or more hydrophobic bases in an amount of about 25% to about 99% by weight of the hydrophobic composition, an amphiphilic compound in an amount of about 0.5% to about 15% by weight of the hydrophobic composition, and a cosolvent in an amount of about 1% to about 20% by weight of the hydrophobic composition. In certain embodiments, two or three or more hydrophobic bases may be present in the hydrophobic composition. Some embodiments include that at least one hydrophobic base may be present in the hydrophobic composition in an amount of about 15% to about 65%, about 25% to about 55%, or about 35% to about 55% by weight of the hydrophobic composition and/or about 1% to about 15%, about 1% to about 10%, or about 1% to about 5% by weight of the hydrophobic composition. The hydrophobic composition may be in the form of an ointment.

In some embodiments, an admixture of the present invention may comprise a hydrophilic composition, which may comprise water, a polymer such as, but not limited to, a charged cellulose or a pharmaceutically acceptable salt thereof, and a humectant, such as, but not limited to, a polyhydric alcohol, in an admixture with a hydrophobic composition, which may comprise at least one hydrophobic base. The hydrophilic composition may be buffered and/or may be in the form of a hydrogel. In some embodiments, the hydrophilic composition may be unbuffered and/or the hydrophilic composition does not comprise or is substantially devoid of a buffer and/or a buffering agent. In some embodiments, the hydrophilic composition may comprise a polymer in an amount of about 0.5% to about 10% by weight of the hydrophilic composition, a humectant in an amount of about 1% to about 20%, and water in an amount of about 70% to about 99%.

In some embodiments, an admixture of the present invention may comprise a buffered hydrogel in admixture with a hydrophobic composition comprising at least one hydrophobic base and an API. The API may comprise a NO-releasing API. The hydrophobic composition may further comprise one or more of an amphiphilic compound, a cosolvent, a humectant, and any combination thereof. In certain embodiments, the admixture may be formed by mixing. In some embodiments, the admixture is self-emulsifying. The admixture may comprise a single phase.

In some embodiments, the hydrophilic composition, the hydrophobic composition, and/or the admixture may be sterilized. Some embodiments include that the hydrophilic composition is sterilized and does not comprise a preservative.

According to embodiments of the present invention, a kit may be provided. In some embodiments, the kit may comprise a first composition and a second composition. The first composition may comprise a hydrophilic composition. The second composition may comprise an API, such as, but not limited to, a NO releasing API. In some embodiments, the second composition may comprise at least one hydrophobic base. In particular embodiments, the second composition comprises an ointment as described herein and/or such as those described in International Application Nos. PCT/US2010/046173 and PCT/US2013/028223, which are incorporated herein by reference in their entirety.

In some embodiments, a kit may comprise a first composition and a second composition that are separately stored. In some embodiments, a kit of the present invention may comprise means for forming an admixture with the first composition and second composition, such as, but not limited to, by mixing, combining, contacting, and the like the compositions prior to application to a subject. A kit may be configured to admix the two compositions upon dispensing and/or for application to a subject. In some embodiments, a kit may be configured to provide an admixture with increased performance and/or activity of the API compared to the performance and/or activity of the API in the absence of one or more of the compositions in the admixture.

In use, an admixture may be formed with a first composition and a second composition and then applied to the skin of a subject, and, in some embodiments, including mucosa. For example, the admixture may be topically administered to one or more of a subject's hand, finger, foot, toe, arm, leg, trunk, anus, genitals, face, a mucous membrane (including a body cavity), nail, etc. In other embodiments, at least one composition in the kit may be applied to the skin of a subject and then at least one different composition in the kit may be applied to same skin of the subject.

In some embodiments, the admixture comprises a first composition comprising a hydrophilic composition and a second composition comprising a hydrophobic composition. The ratio of the hydrophilic composition to the hydrophobic composition may be about 5:1 or less, in further embodiments, about 4:1 or less, about 3:1 or less, about 2:1 or less or about 1:1. In certain embodiments, the ratio is about 3:1. In further embodiments, the ratio is about 1:1. The admixture may be applied to a subject in such a ratio. In certain embodiments, a kit of the present invention comprises means for dispensing and/or delivering the first and second compositions in the appropriate amounts to achieve the desired ratio. In some embodiments, the ratio of the first composition and second composition in the admixture may be adjusted and/or modified to achieve a desired API release pattern.

Providing a hydrophilic composition and a hydrophobic composition that are admixed upon application to the skin of a subject may allow for a longer shelf life of a kit of the present invention than if the compositions were stored and/or mixed together in the kit. For example, the formulation and loading of an API in a hydrophobic composition may provide a stable product with a long shelf life. Thus, for example, pH and/or water content of the hydrophobic composition may be adjusted to reduce or minimize release of the API, such as a water activated API, so as to provide a composition that is stable at room temperature. The hydrophilic composition may then be combined with the hydrophobic composition to adjust the combined pH and/or provide water to activate the API. The hydrophobic composition may be combined with the hydrophilic composition in differing ratios to provide a desired release, pH and/or dose in the admixture. Such an approach may allow for a single manufacturing process to be utilized for production of a more complex and costly hydrophobic composition and then particular products defined by the composition and/or quantity of the hydrophilic composition with which the hydrophobic composition is mixed.

As used herein, the term "shelf life" refers to the length of time a product (e.g., a composition and/or kit of the present invention) maintains the ability to release a therapeutically effective amount of an API, such as, but not limited to, nitric oxide, in an unopened package stored under recommended storage conditions. The shelf life may, for example, be evidenced by the "use by" or "best if used by" date for the product, the manufacturer's expiration date of the product and/or the actual product characteristics after the specified period of time. Accordingly, the term "shelf life" as used herein should be construed as including both an "actual" shelf life of the product and a "predicted" shelf life of the product unless stated otherwise. As one skilled in the art will recognize, the rate of release of nitric oxide in a composition under packaged and/or stored conditions may be different (i.e., faster or slower) than the rate of release of nitric oxide when the composition is in use (e.g., when the composition comprising the NO-releasing API is in admixture with another composition). In certain embodiments, the rate of release of nitric oxide from a composition of the present invention may be more rapid when the composition is in use compared to the rate of release of nitric oxide when a composition comprising the API was packaged and/or stored.

In some embodiments, the shelf life of the product is the time that the product maintains the ability to release at least 50% of the initial amount of nitric oxide that the product may release when packaged. In further embodiments, the shelf life of the product is the time that the product maintains the ability to release at least 70%, at least 80%, at least 90%, at least 95%, or at least 98% of the initial amount of nitric oxide that the product may release when packaged. In some embodiments, the shelf life of the product is the time that the product maintains the ability to release a therapeutically effective amount of nitric oxide over a desired period of time. In some embodiments, the recommended storage conditions are room temperature. In some embodiments, the recommended storage conditions are refrigerated storage conditions. In particular embodiments, the refrigerated storage conditions are between $1°C.-12°C.$, or any range and/or individual value therein.

Further embodiments may provide packaged compositions of the present invention that have a useful life of at least about 7 days after opening the package. In further embodiments, the useful life is at least about 30 days, at least about 60 days or at least about 90 days. In still further embodiments, the packaged compositions have a useful life of from at least about 60 days to at least about 730 days. As used herein, the term "useful life" refers to the length of time that the product maintains the ability to release a therapeutically effective amount of nitric oxide from an opened packaged when applied as recommended and when stored under recommended storage conditions. The useful life may, for example, be evidenced by the manufacturer's recommended time to dispose of the product after opening or measurements of the products characteristics after opening.

Accordingly, the term "useful life" as used herein should be construed as including both an "actual" useful life of the product or a "predicted" useful life of the product unless stated otherwise. In some embodiments, the useful life of the product is the time that the product maintains the ability to release at least 50% of the initial amount nitric oxide that the product may release when the package is opened. In further embodiments, the useful life of the product is the time that the product maintains the ability to release at least 70%, at least 80%, at least 90%, at least 95%, or at least 98% of the initial amount nitric oxide that the product may release when the package is opened. In some embodiments, the recommended storage conditions after opening are room temperature. In particular embodiments, the recommended storage conditions after opening are refrigerated conditions.

As will be appreciated by those of skill in the art in light of the present disclosure, a hydrophilic composition, such as those described herein, may provide means for adjusting the pH of a pharmaceutical composition as well as means for activating an API of a pharmaceutical composition. In some embodiments, a hydrogel, such as those described herein, may provide means for maintaining and/or stabilizing the pH of a hydrophobic composition when used to form an admixture with the hydrogel. Means for maintaining and/or stabilizing the pH of an admixture may be configured to activate and/or initiate release of an API. In particular embodiments, a hydrogel of the present invention may provide means for maintaining and/or stabilizing the pH of an admixture comprising a diazeniumdiolate modified co-condensed polysiloxane macromolecule. In some embodiments, the pH may be maintained and/or stabilized within a pH range of about 5 to about 8. In further embodiments, a hydrogel of the present invention may provide means for releasing nitric oxide from a pharmaceutical composition comprising a diazeniumdiolate modified co-condensed polysiloxane macromolecule.

According to some embodiments, a method of the present invention comprises administering a composition of the present invention to the skin of a subject, including mucosa. For example, the composition may be administered to one or more of a subject's hand, finger, foot, toe, arm, leg, trunk, anus, genitals, face, a mucous membrane (including a body cavity), nail, etc. In certain embodiments, the composition may be topically administered. In some embodiments, a hydrophilic composition of the present invention may be topically administered to the skin of a subject. In certain embodiments, an admixture comprising a hydrophobic composition and a hydrophilic composition may be topically administered to the skin of a subject. The admixture may comprise at least one API, such as, but not limited to, a NO-releasing API.

A method of the present invention may comprise forming an admixture prior to and/or during the administering step. An admixture may be prepared by mixing, blending, contacting, applying to a same area or region, emulsifying, and the like a hydrophilic composition such as, but not limited to, a hydrogel, and a hydrophobic component such as, but not limited to an ointment.

In some embodiments, a method of the present invention comprises delivering a therapeutically effective amount of nitric oxide to the skin of a subject. As used herein, the term "therapeutically effective amount" refers to an amount of an API, such as, but not limited to, nitric oxide, that elicits a therapeutically useful response in a subject. Those skilled in the art will appreciate that the therapeutic effects need not be complete or curative, as long as some benefit is provided to the subject.

The present invention finds use in both veterinary and medical applications. Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and canaries), and birds in ovo.

The methods of the present invention may also be carried out on animal subjects, particularly mammalian subjects such as mice, rats, dogs, cats, livestock and horses for veterinary purposes, and/or for drug screening and drug development purposes.

In particular embodiments of the present invention, the subject is "in need of" a method of the present invention, e.g., the subject has been diagnosed with, is at risk for, and/or is believed to have a disease or disorder that may be treated using a method of the present invention. In some embodiments, the subject has a skin disorder, such as, but not limited to, acne, atopic dermatitis, and/or psoriasis. In other embodiments, the subject has a wound, such as, but not limited to, a bed sore, a burn, a chronic venous leg ulcer, and/or a diabetic foot ulcer. In some embodiments of the present invention, the subject has an inflammatory skin condition or disorder. In some embodiments of the present invention, the subject has an infection, such as a viral, bacterial or fungal infection and, in particular embodiments, an infection with a cutaneous symptom. In some embodiments, the subject has a cosmetic condition, such as a scar, crow's feet, etc. In still further embodiments, the subject has a cancer of the skin.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom is achieved and/or there is a delay in the progression of the disease or disorder. In particular embodiments, the severity of a skin disorder may be reduced in a subject compared to the severity of the skin disorder in the absence of a method of the present invention. In other embodiments, a method of the present invention may improve wound healing and/or prevent against infection.

A composition of the present invention may be applied topically to any portion of a subject's skin. However, in some embodiments, the subject's face is treated by a method described herein. Furthermore, in some embodiments, the subject's trunk is treated by a method described herein. In certain embodiments, a composition of the present invention is applied to a wound present on a subject.

According to some embodiments, a method of increasing the release of nitric oxide from a hydrophobic composition containing a diazeniumdiolate modified macromolecule may be provided. The method may comprise forming an admixture; and applying the admixture to the skin of a subject. The admixture may comprise at least one hydrophilic composition and at least one hydrophobic composition comprising the diazeniumdiolate modified macromolecule. In some embodiments, the hydrophilic composition may have a pH of about 4 to about 6. The forming step or admixing step may be carried out on the skin of the subject or may be carried out prior to application of the admixture to the skin of the subject.

A method of the present invention may increase the amount of nitric oxide released by at least about 10%, 20%, 30%, 40%, 50%, 60%, 70%, 80%, 90, 100%, 150%, 200%, 300%, 400%, or more, or any range and/or individual value therein compared to the amount of NO released in the absence of a method of the present invention over the same period of time. A method of the present invention may provide a NO release that is increased by about 1.5 to about 100 times than the amount of NO released in the absence of a method of the present invention over the same period of time or any range and/or individual value therein, such as, but not limited to by about 2 to about 10 times or by about 5 to about 50 times.

In further embodiments, a method of providing a topical antimicrobial composition may be provided. The method may comprise forming an admixture; and applying the admixture to the skin of a subject. The admixture may comprise at least one hydrophilic composition and at least one hydrophobic composition. In some embodiments, the hydrophobic composition may comprise a diazeniumdiolate modified macromolecule. In some embodiments, the hydrophilic composition may have a pH of about 4 to about 6. The forming step or admixing step may be carried out on the skin of the subject or may carried out prior to application of the admixture to the skin of the subject. A method of the present invention may inhibit the growth of a pathogen, such as by about 5%, 10%, 20%, 30%, 40%, 50%, 60%, 70%, 80%, 90, 100%, 150%, 200%, or more compared to the growth of a pathogen in the absence of a method of the present invention.

A method of increasing the rate of healing for a wound may also be provided. The method may comprise applying topically an admixture of the present invention to a wound. The admixture may comprise at least one hydrophilic composition and at least one hydrophobic composition. In some embodiments, the hydrophobic composition may comprise a diazeniumdiolate modified macromolecule. In some embodiments, the hydrophilic composition may have a pH of about 4 to about 6. The admixture may be antimicrobial and/or may be configured to buffer the wound to a pH below 7. In some embodiments, a method of the present invention may increase the rate of healing for a wound by at least about 5%, 10%, 20%, 30%, 40%, 50%, 60%, 70%, 80%, 90, 100%, 150%, 200%, or more compared to the rate of healing from a similar wound in the absence of a method of the present invention and/or compared to the rate of healing from a similar wound for which a conventional topical treatment is applied (e.g., triple antibiotic ointment). In some embodiments, a method of the present invention may increase tissue oxygen availability and/or reduce the histotoxicity of a bacterial end product.

A composition, kit, and/or method of the present invention may minimize and/or prevent degradation of at least one API such as, but not limited to, a NO-releasing API. In some embodiments, a composition of the present invention may be configured to provide a repeatable rate and/or pattern of NO release to a variety of therapeutic sites with varying moisture contents. In certain embodiments, a composition of the present invention may be configured to provide a rate of NO release that is independent of the moisture content present at a therapeutic site.

The present invention is explained in greater detail in the following non-limiting Examples.

EXAMPLES

Example 1

An in vitro test comparing the release of nitric oxide from an ointment in combination with different hydrophilic phases was performed. The ointment was combined with either wet nitrogen (i.e., neat), water in a 1:2 ratio (ointment:water) or a hydrogel in a 1:1 ratio. The formulation for the ointment and hydrogel are provided in Table 1.

TABLE 1

Ointment and hydrogel formulation.

| Ointment | % | Hydrogel | % |
|---|---|---|---|
| Crodabase SQ, Mineral Oil/Polyethylene | 55.5 | Anhydrous Glycerol | 10.0 |

TABLE 1-continued

Ointment and hydrogel formulation.

| Ointment | % | Hydrogel | % |
|---|---|---|---|
| Light Mineral oil | 13.5 | Triethanolamine | 1.2 |
| Miglyol 812 Caprylic/Capric Triglyceride | 12.0 | Carbopol ® 974P, Carbomer Homopolymer Type A | 0.6 |
| Softigen 767 PEG-6-Caprylic/Capric Glycerides | 10.0 | Deionized Water | 88.2 |
| Hexylene glycol | 8.0 | | |
| Nitricil ™ NVN1 | 1.0 | | |
| Total | 100 | Total | 100 |

The in vitro test of the nitric oxide release showed a significant difference before and after addition of the hydrophilic phase even in carrier gas with full moisture content. The hydrophilic phase's ability to promote the nitric oxide release from the hydrophobic phase, especially at a lower Nitricil™ NVN1 loading, is significantly higher than water alone. While not wishing to be bound to any particular theory, the results suggest that the efficiency to provide access of protons to the drug substance in the hydrophobic phase increases remarkably with the excipients of emollient and solubilizing capacities (Table 2).

TABLE 2

Nitric oxide release from a 1% Nitricil ™ NVN1 ointment in combination with different hydrophilic phases.

| Parameter | Wet $N_2$ | Water | Hydrogel |
|---|---|---|---|
| Ointment Sample Weight (mg) | 52.0 | 44.2 | 46.2 |
| Cmax (ppb) | 307.0 | 2,600.0 | 13,700.0 |
| Tmax (min) | 6.7 | 30.0 | 1.1 |
| Total Nitric Oxide Release in First Hour (PPB) | 976,055.0 | 4,385,884.0 | 14,926,266.0 |
| Total Nitric Oxide Release in First Hour per Sample Weight (PPB/mg) | 18,770.0 | 99,228.0 | 323,079.4 |

The results demonstrate that the hydrogel works well in promoting nitric oxide release from the hydrophobic ointment with lower Nitricil™ NVN1 loading. However, when the potency for the drug product increases, the release kinetics do not follow the loading capacity (i.e., the nitric oxide release does not increase proportionally with the percentage of the drug substance). The sluggish release becomes more significant with the higher drug substance loading over 10% by weight. While not wishing to be bound to any particular theory, it is believed that the pH of the final formulation is too high for the higher loading drug product to release effectively.

Example 2

It was discovered by the present inventors that in order to maintain a controlled release of nitric oxide from the drug product at different loadings, the concentration of the key reagent, proton, needs to be maintained. This means that the final pH of a composition comprising a hydrophilic phase (e.g., a hydrogel) and a hydrophobic phase (e.g., an ointment) needs to stay within a specified range across different potencies. To achieve this, the hydrophilic phase of the composition can be designed to have a larger buffer capacity than the hydrophobic phase at the highest target drug product potency.

In order to have both a large buffer capacity and a desired range of the final formulation at pH 5-8, phosphoric acid monobasic was selected as a buffer for the hydrogel. For the $[H_2PO_4]^-$ ion, the pKa is 7.2. According to the Henderson-Hasselbalch equation (Equation 1), the pH of the solution at an equal concentration of the acid and base will be in the optimal neutral condition as the drug product, (pH=7.2), giving it a large buffer capacity.

Henderson-Hasselbalch equation.

$$pH = pK_a + \log\left(\frac{[A^-]}{[HA]}\right)$$ Equation 1

A hydrogel with 400 mmol of phosphoric acid monobasic (i.e., phosphate buffered hydrogel) and having a pH value of 4.8(+/−0.1) was prepared (Table 3). The hydrogel was then mixed with a Nitricil™ NVN4 ointment having a 0.9% weight of nitric oxide loading to determine the nitric oxide release results. Table 3 provides the formulations for the ointment and hydrogel.

TABLE 3

Ointment and hydrogel formulations.

| Ointment | % | Phosphate Buffered Hydrogel | % |
| --- | --- | --- | --- |
| Crodabase SQ, Mineral Oil/Polyethylene | 55.9 | Water, deionized | 71.8 |
| Light Mineral oil | 4.7 | Potassium phosphate monobasic | 5.2 |
| Miglyol 812 Caprylic/Capric Triglyceride | 11.9 | Hexylene glycol | 19 |
| Softigen 767 PEG-6-Caprylic/Capric Glycerides | 9.9 | Hydroxyethyl cellulose ethoxylate, quaternized | 3 |
| Hexylene glycol | 7.9 | | |
| Nitricil ™ NVN4 | 9.7 | | |
| Total | 100 | Total | 100 |

When the phosphate buffered hydrogel was mixed with the ointment, the pH increased, but to a much lesser degree compared to the hydrogel formulation without phosphate described in Example 1. Table 4 provides the in vitro nitric oxide release results of combined ointment/phosphate buffered hydrogel at three different NO loadings. The combined ointment/phosphate buffered hydrogel is compared to two separate combinations of the ointment with one of two non-buffered hydrogel formulations at different pH values. The non-buffered hydrogel formulations have a composition as set forth in Table 1 and a pH of 4 and 6, respectively. The results clearly show that the phosphate buffered hydrogel can stabilize the final formulation pH at the desired range, and promote high levels of nitric oxide release across all three loadings.

TABLE 4

In vitro nitric oxide release and pH data for Nitricil ™ NVN4 ointment admixtures.

| Ointment | Hydrophilic Phase | $C_{max}$ pmol/mg | Cumulative NO nmol/mg | pH |
| --- | --- | --- | --- | --- |
| 3.2% Nitricil ™ NVN4 | Phosphate Buffered Hydrogel pH 4.8 (Phogel48) | 30 | 54 | 6.1 |
| (0.3% NO) | Nonbuffered pH 4 (AH-002) | 13 | 39 | 6.1 |
| | Nonbuffered pH 6 (AH-001) | 9.8 | 16 | 9.1 |
| 9.7% Nitricil ™ NVN4 | Phosphate Buffered Hydrogel pH 4.8 (Phogel48) | 30 | 108 | 6.9 |
| (0.9% NO) | Nonbuffered pH 4 (AH-002) | 6.6 | 48 | 9.0 |
| | Nonbuffered pH 6 (AH-001) | 2.6 | 23.2 | 9.9 |
| 19.4% Nitricil ™ NVN4 | Phosphate Buffered Hydrogel pH 4.8 (Phogel48) | 13 | 114 | 7.9 |
| (1.8% NO) | Nonbuffered pH 4 (AH-002) | 6.8 | 62.0 | 9.5 |
| | Nonbuffered pH 6 (AH-001) | 5.9 | 25.5 | 10.1 |

Example 3

A comparison of the nitric oxide release from a Nitricil™ NVN4 ointment with a 1.8% NO loading in the absence of and with different moisture sources (i.e., hydrophilic phases) was performed. The ointment formulation is provided in Table 3. Two different moisture sources were combined with the ointment. The first source was a neutral hydrogel with a pH of 6 and having a formulation as described in Example 1, Table 1, and the second was a phosphate buffered hydrogel having a formulation as described in Example 2, Table 3. FIG. 1 shows the NO release from the ointment alone and the NO release the ointment/hydrophilic phase admixtures, and the results are shown in Table 5.

TABLE 5

NO release parameters for different formulations containing Nitricil ™ NVN4 ointment (1.8% w/w NO).

| Hydrophobic Phase | Hydrophilic Phase | $C_{max}$ (pmol/mg) | Cumulative NO (nmol/mg) | $T_{50}$ (min) |
| --- | --- | --- | --- | --- |
| Ointment | N/A | 0.55 | 29 | 777 |
| Ointment | Neutral Hydrogel (AH-001) | 1.6 | 95 | 609 |
| Ointment | Phosphate Buffered Hydrogel (Phogel48) | 15.2 | 191 | 421 |

Example 4

Three Nitricil™ NVN4 ointment formulations having different NO loadings were each combined with a phosphate buffered hydrogel in a 1:1 ratio to form an admixture. The formulations for the ointment and hydrogel are provided in Table 6.

TABLE 6

Ointment and hydrogel formulations.

| Ointment Formulation (TO-007) | | | | Hydrogel Formulation (Phogel48) | |
|---|---|---|---|---|---|
| Component | 3.2% | 9.7% | 19.4% | Component | % |
| Crodabase SQ, Mineral Oil/Polyethylene | 61.1 | 55.9 | 48.9 | Water, deionized | 71.8 |
| Light Mineral oil | 6.0 | 4.7 | 2.0 | Potassium phosphate monobasic | 5.2 |
| Miglyol ® 812 Caprylic/Capric Triglyceride | 11.9 | 11.9 | 11.9 | Hexylene glycol | 19 |
| Softigen ® 767 PEG-6-Caprylic/Capric Glycerides | 9.9 | 9.9 | 9.9 | Hydroxyethyl cellulose ethoxylate, quaternized | 3.0 |
| Hexylene glycol | 7.9 | 7.9 | 7.9 | | |
| Nitricil ™ NVN4 | 3.2 | 9.7 | 9.7 | | |
| Total | 100 | 100 | 100 | Total | 100 |

The vehicle ointment did not contain the drug product, Nitricil™ NVN4, but contained all other components in the Nitricil™ NVN4 ointment formulations. Mupirocin was used as a positive control. These formulations (i.e., the test articles) were then tested for efficacy against MRSA *Staphylococcus aureus* in a porcine animal model. ATCC BAA 1686 bacterial counts were taken on days 4 and 7 after treatment application.

Figure 2:
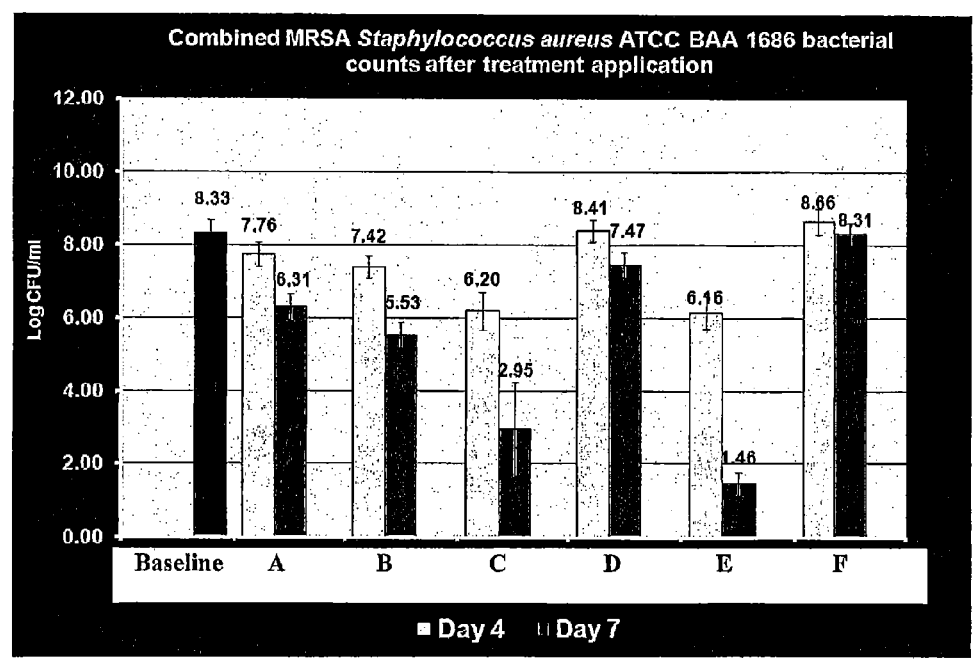
FIG. 2 shows a graph of the combined MRSA *Staphylococcus aureus* ATCC BAA 1686 bacterial counts after treatment application on days 4 and 7.
Figure 3:
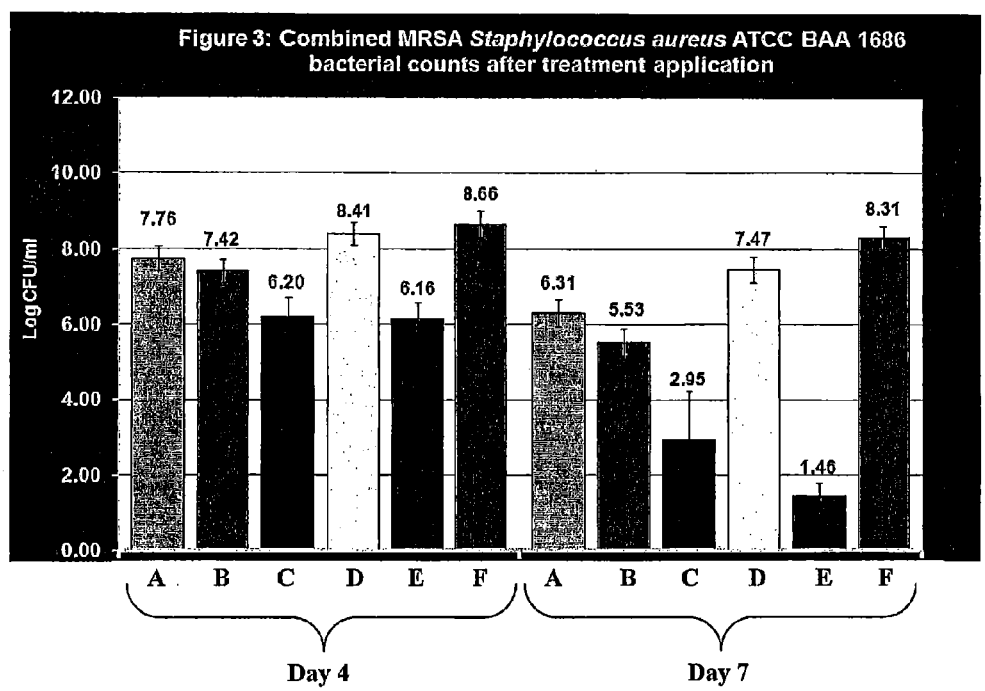
FIG. 3 shows a graph of the combined MRSA *Staphylococcus aureus* ATCC BAA 1686 bacterial counts after treatment application on days 4 and 7.

Three specific pathogen-free pigs (Looper Farms, N.C.) were anesthetized and 51 rectangular wounds (10 mm×7 mm×0.5 mm deep) were made to the paravertebral and thoracic area with an elecrokeratome. Wounds were separated by 15 mm of unwounded skin and individually dressed. Eight wounds were randomly assigned to each treatment group (6) and baseline. A fresh culture of *S. aureus* strain BAA-1686 was prepared from a TSA plate grown overnight at 37° C. *S. aureus* from the overnight culture was resuspended in 4.5 ml of saline until a solution corresponding to $10^{10}$ CFU/ml was obtained. Serial dilution was performed to create an initial inoculum concentration of $10^6$ CFU/ml was achieved. 25 μl of the inoculum suspension was inoculated into each wound by scrubbing with a sterile spatula for 10 seconds. All wounds were covered individually with a polyurethane film dressing (TEGADERM™). The bacterial biofilms were allowed to form for 48 hours prior to treatment. Treatment groups were treated with approximately 200 mg of test article and spread out to cover the wound and surrounding unwounded area with a sterile spatula and covered with film dressing. At the assessment time, 4 wounds per treatment group were recovered in 1 ml of neutralization solution and serially diluted. Serial dilutions were subsequently plated on Oxacillin Resistance Screening Agar (ORSA) and incubated for 24 hours at 37° C. prior to enumeration of viable colonies. The MRSA BAA-1686 bacterial counts following treatment are provided in FIGS. 2 and 3.

While not wishing to be bound to any particular theory, the data suggest that Nitricil™ macromolecules exhibit robust antimicrobial activity against biofilm-embedded *S. aureus*. Unlike traditional antibiotics, Nitricil™ NVN4 was effective at reducing biofilm populations. Nitricil™ macromolecules may be an effective therapy for the treatment of chronic *S. aureus* infections and may be an efficacious antimicrobial agent in vivo using a partial thickness wound model.

Example 5

Ointment formulations were prepared as follows in Tables 7 and 8, which list the percent of each component by weight of the respective ointment formulation. Buffered hydrogel formulations were prepared as follows in Table 9, which lists the percent of each component by weight of the respective buffered hydrogel formulation and pH of each buffered hydrogel formulation.

TABLE 7

Composition of example ointment formulations.

| Component | TO-008 | TO-009 | TO-010 | TO-011 | TO-012 | TO-013 | TO-014 | TO-015 | TO-016 | TO-018 |
|---|---|---|---|---|---|---|---|---|---|---|
| PEG400 | — | 89.0 | — | — | — | 20.0 | 20.0 | — | 38.0 | — |
| Crodabase SQ | 60.0 | — | 79.0 | 60.0 | 60.0 | 60.0 | 60.0 | 60.0 | 60.0 | 53.0 |
| Petrolatum, White | — | — | — | — | — | — | — | — | — | 15.0 |
| Light Mineral Oil | 13.0 | — | 8.0 | 11.0 | 11.0 | 13.0 | 13.0 | — | — | — |
| Mineral Oil | — | — | — | — | — | — | — | 13.0 | — | 10.0 |
| Miglyol ® 812 | 12.0 | — | 6.0 | 12.0 | 12.0 | — | — | 12.0 | — | 12.0 |
| Miglyol ® 840 | — | — | — | — | 10.0 | — | — | — | — | — |
| Cyclomethicone | — | — | — | 10.0 | — | — | — | — | — | — |
| PEG 3350 | — | 9.0 | — | — | — | — | — | — | — | — |
| Hexylene Glycol | 8.0 | — | — | — | — | — | — | 8.0 | — | — |
| Cetyl Alcohol | — | — | — | — | — | — | — | — | — | 8.0 |
| Softigen ® 767 | 5.0 | — | 5.0 | 5.0 | 5.0 | — | 5.0 | 5.0 | — | 2.0 |
| Nitricil ™ NVN1 | 2.0 | 2.0 | 2.0 | 2.0 | 2.0 | 2.0 | 2.0 | 2.0 | 2.0 | 2.0 |

TABLE 8

Composition of further example ointment formulations.

| Component | \multicolumn{10}{c}{TO-017} |
|---|---|---|---|---|---|---|---|---|---|---|

| Component | A | B | C | D | E | F | G | H | I | J |
|---|---|---|---|---|---|---|---|---|---|---|
| Crodabase SQ | — | 26.7 | 40.0 | 13.3 | 0.00 | 80.0 | 13.3 | 40.0 | 53.4 | — |
| Petrolatum, White | — | 26.7 | 40.0 | 13.3 | 40.0 | — | 53.4 | — | 13.3 | 80.0 |
| Cetyl Alcohol | 80.0 | 26.6 | — | 53.4 | 40.0 | — | 13.3 | 40.0 | 13.3 | — |
| Miglyol ® 812 | 12.0 | 12.0 | 12.0 | 12.0 | 12.0 | 12.0 | 12.0 | 12.0 | 12.0 | 12.0 |
| Mineral Oil | 4.0 | 4.0 | 4.0 | 4.0 | 4.0 | 4.0 | 4.0 | 4.0 | 4.0 | 4.0 |
| Softigen ® 767 | 2.0 | 2.0 | 2.0 | 2.0 | 2.0 | 2.0 | 2.0 | 2.0 | 2.0 | 2.0 |
| Nitricil™ NVN1 | 2.0 | 2.0 | 2.0 | 2.0 | 2.0 | 2.0 | 2.0 | 2.0 | 2.0 | 2.0 |

TABLE 9

Composition of example buffered hydrogel formulations.

| Component | Unbuffered AH-010 (pH 6) | Buffered | | | | | |
|---|---|---|---|---|---|---|---|
| | | CA-001 (pH 5.5) | CA-002 (pH 6.5) | CA-003 (pH 5.5) | PHO-002 (pH 5) | PHO-003 (pH 6) | PHO-004 (pH 7) |
| Purified Water | 87.1 | 83.0 | 83.0 | 83.7 | 80.6 | 85.0 | 73.5 |
| Glycerin | 10.0 | 10.0 | 10.0 | 10.0 | 10.0 | 10.0 | 10.0 |
| Potassium Phosphate Monobasic | — | — | — | — | 5.9 | 1.3 | 5.8 |
| Potassium Phosphate Dibasic | — | — | — | — | — | 0.2 | 7.2 |
| Carboxymethylcellulose Sodium | 2.8 | 4.0 | — | 1.5 | 3.5 | 3.5 | 3.5 |
| Sodium Alginate | — | — | 4.0 | — | — | — | — |
| Citric Acid, Anhydrous | — | 2.0 | 1.8 | 1.8 | — | — | — |
| Sodium Hydroxide | — | 0.8 | 1.0 | 1.0 | — | — | — |
| Phenoxyethanol | — | — | — | 0.6 | — | — | — |
| Trolamine | — | — | — | 0.6 | — | — | — |
| Carbopol ® 974P | — | — | — | 0.4 | — | — | — |
| Sorbic Acid | — | 0.2 | — | — | — | — | — |
| Benzoic Acid | 0.1 | — | — | — | — | — | — |
| Methylparaben | — | — | 0.1 | 0.2 | — | — | — |
| Propylparaben | — | — | 0.1 | — | — | — | — |
| Total | 100.0 | 100.0 | 100.0 | 100.0 | 100.0 | 100.0 | 100.0 |

Example 6

Three specific pathogen-free pigs (Looper Farms, N.C.) per microorganism were anesthetized and 51 rectangular wounds (10 mm×7 min×0.5 mm deep) were made to the paravertebral and thoracic area with an elecrokeratome. Wounds were separated by 15 mm of unwounded skin and individually dressed. Eight wounds were randomly assigned to each treatment group and baseline. After creation of the burns/wounds, 25 µl of *Acinetobacter baumannii* (AB 09-001*), Methicillin Resistant *S. aureus* (MRSA USA300) and *Candida albicans* (CA 09-024*) were use to inoculate each wound by scrubbing ($10^6$ CFU/ml) inoculums into each wound with a teflon spatula for approximately 30 seconds. All wounds were covered individually with a polyurethane film dressing (TEGADERM™). The bacterial biofilms were allowed to form for 48 hours prior to treatment.

Treatment groups were treated with approximately 200 mg of test article and spread out to cover the wound and surrounding unwounded area with a sterile spatula and covered with the film dressing. The test articles include the three Nitricil™ NVN4 ointment formulations having different NO loadings described in Table 6 of Example 4, which were each combined with the phosphate buffered hydrogel described in Table 6 of Example 4. The vehicle ointment did not contain the drug product, Nitricil™ NVN4, but contained all other components in the Nitricil™ NVN4 ointment formulations. Silver sulfadiazine was used as a positive control.

Figure 4:
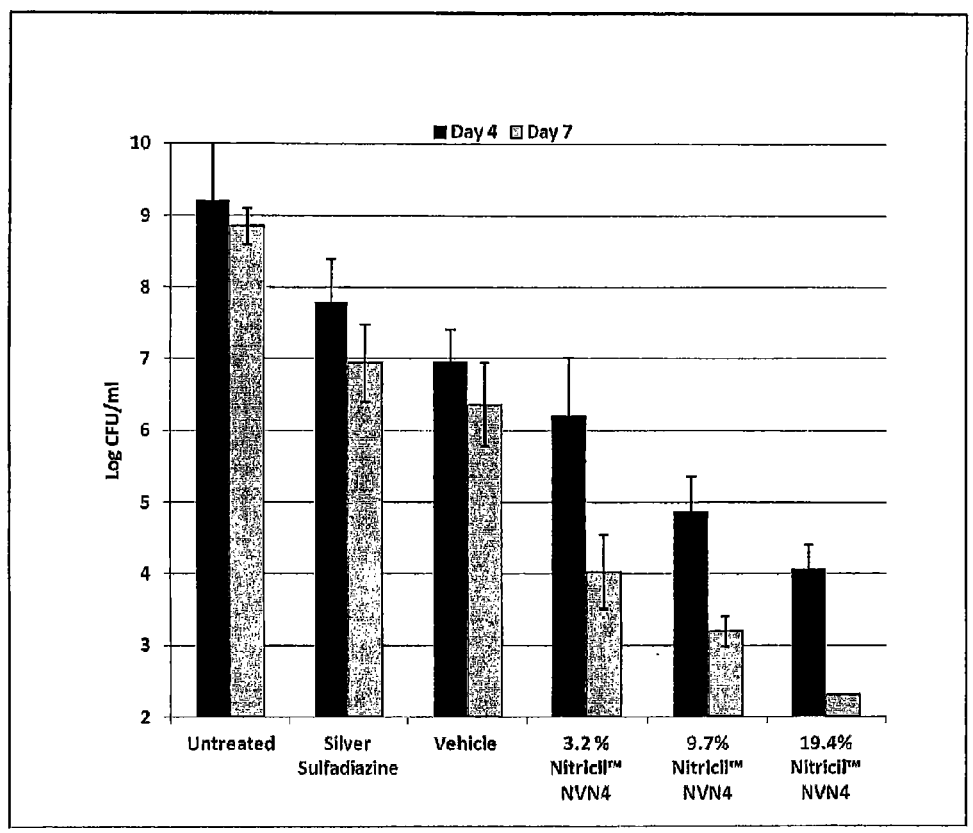
FIG. 4 shows a graph of the *A. baumannii* bacterial counts after treatment application on days 4 and 7.
Figure 5:
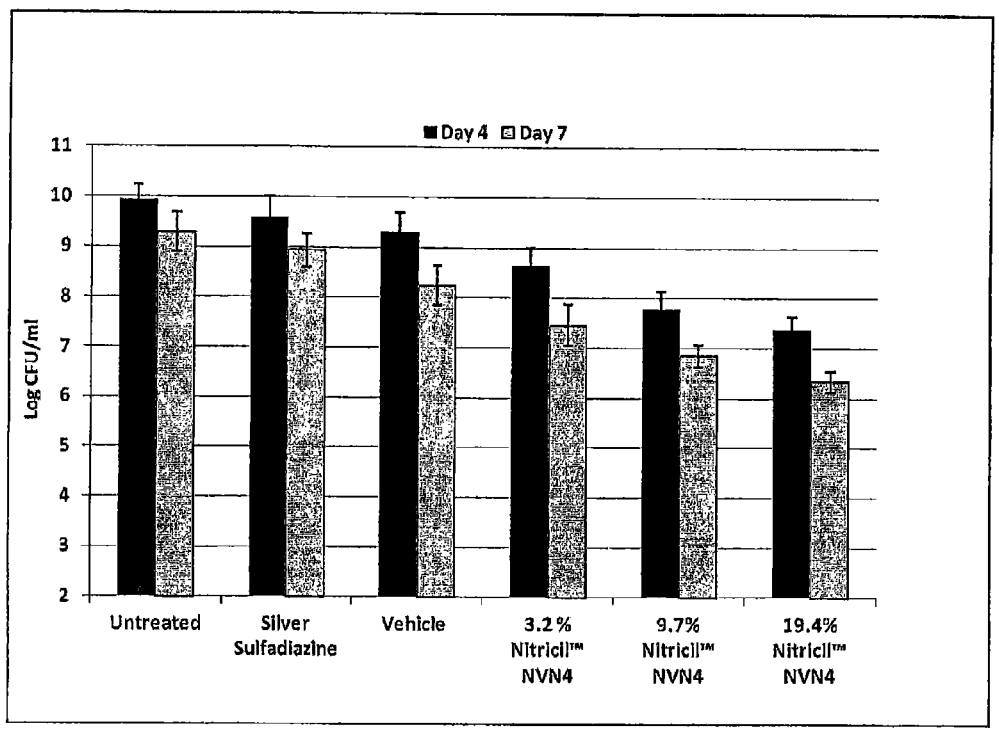
FIG. 5 shows a graph of the *S. aureus* bacterial counts after treatment application on days 4 and 7.
Figure 6:
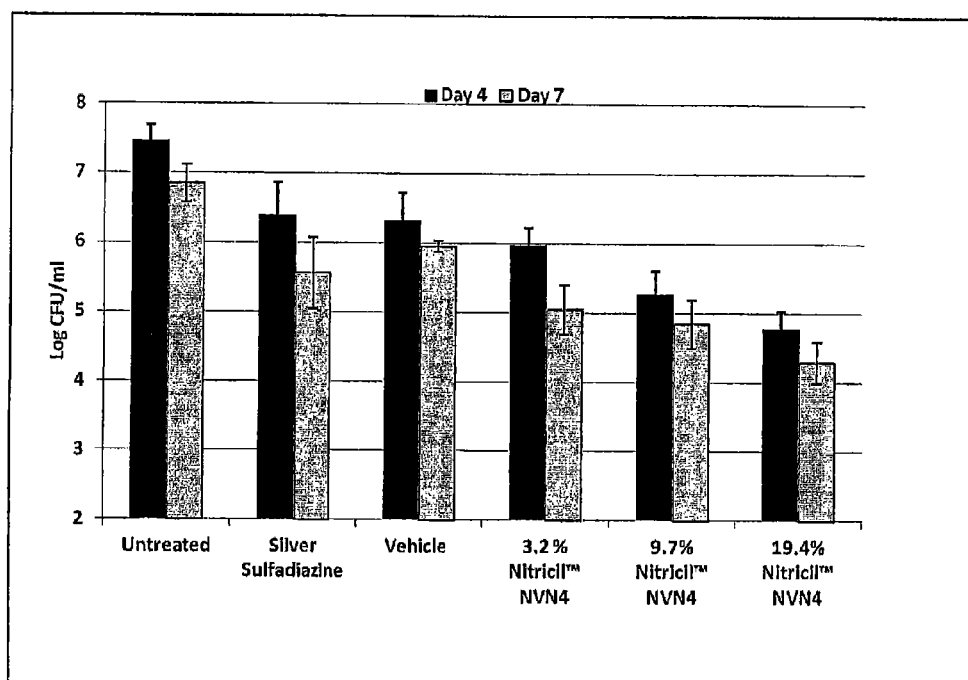
FIG. 6 shows a graph of the *C. albicans* bacterial counts after treatment application on days 4 and 7.

At the assessment time, 4 wounds per treatment group were recovered in 1 ml of neutralization solution and serially diluted. Serial dilutions were subsequently plated on selective media and incubated for 24 hours at 37° C. prior to enumeration of viable colonies. Colonies were counted and the colony forming units per ml (CFU/ml), Log CFU/ml, mean Log CFU/ml and standard deviation calculated. A one-way analysis of variance (ANOVA) was used for statistical analysis. A p value of less than 0.05 was considered significant. FIG. 4 shows the results for *A. baumannii*, FIG. 5 shows the results for *S. aureus*, and FIG. 6 shows the results for *C. albicans*.

While not wishing to be bound to any particular theory, the data suggest that Nitricil™ macromolecules are an effective antibacterial against biofilm-embedded *A. bauman-* nii, *S. aureus*, and *C. albicans*. Thus, Nitricil™ macromolecules may be an effective therapy for the treatment of chronic *A. baumannii*, *S. aureus*, and *C. albicans* infections and may be an efficacious antimicrobial agent in vivo using a partial thickness wound model.

Example 7

The release of nitric oxide from three different admixtures was compared. The admixtures were formed with an ointment formulation, TO-007b as provided in Table 10, having varying concentrations of Nitricil™ NVN4 and a hydrogel formulation, Phogel48 as provided in Table 6 of Example 4. The ointment formulations had 3.2% Nitricil™ NVN4 (0.3% NO content), 6.4% Nitricil™ NVN4 (0.9% NO content), or 12.8% Nitricil™ NVN4 (1.8% NO content) and were combined with the hydrogel in a 1:1 ratio.

TABLE 10

Ointment formulation.

| | Ointment Formulations (TO-007b) | | |
|---|---|---|---|
| Component | 3.2% Nitricil™ NVN4 | 6.4% Nitricil™ NVN4 | 12.8% Nitricil™ NVN4 |
| Crodabase SQ | 60.0 | 60.0 | 58.0 |
| Miglyol ® 812 | 12.0 | 12.0 | 12.0 |
| Hexylene glycol | 8.0 | 8.0 | 8.0 |
| Softigen ® 767 | 5.0 | 5.0 | 5.0 |
| Light Mineral Oil | 11.8 | 8.6 | 4.2 |
| Nitricil™ NVN4 | 3.2 | 6.4 | 12.8 |
| Total | 100 | 100 | 100 |

Figure 7:
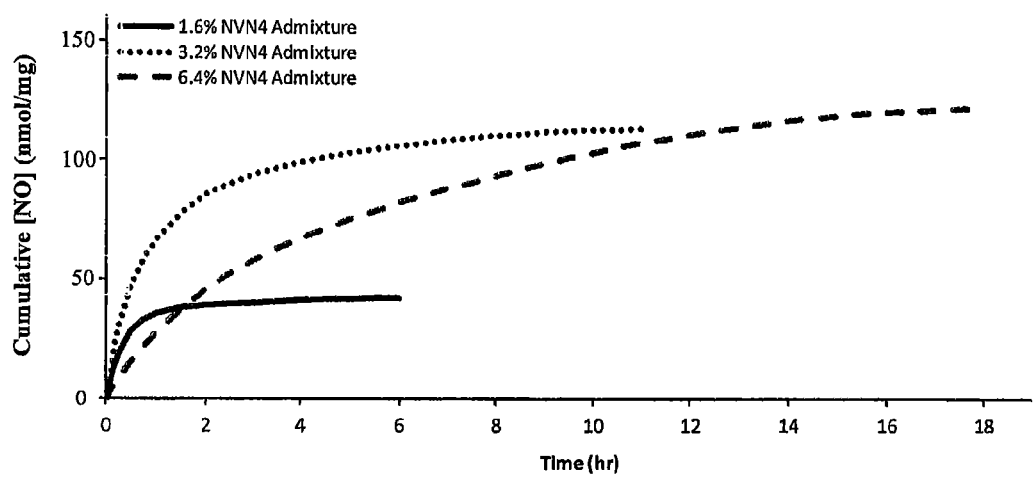
FIG. 7 shows a graph of the cumulative nitric oxide (NO) release over time for each of the three admixtures.
Figure 8:
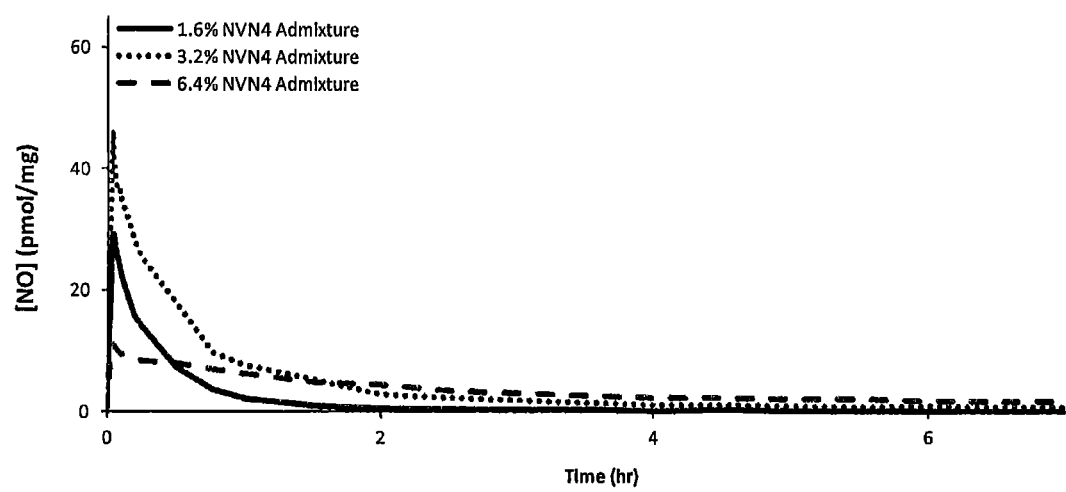
FIG. 8 shows a graph of the real time NO release over time for each of the three admixtures.

The real time NO release and cumulative NO for the different admixtures are provided in Table 11. The cumulative NO release over time for the admixtures is provided in FIG. 7 and the real-time concentration of NO release over time for the admixtures is provided in FIG. 8.

TABLE 11

Admixture NO release properties.

| Time (hr) | Real-Time NO Release (pmol/mg) | | | Time (hr) | Cumulative NO (nmol/mg) | | |
|---|---|---|---|---|---|---|---|
| | 3.2% | 6.4% | 12.8% | | 3.2% | 6.4% | 12.8% |
| 0.50 | 7.15 | 17.63 | 7.89 | 0.50 | 28.13 | 46.90 | 15.33 |
| 1.0 | 2.03 | 7.47 | 6.18 | 1.0 | 35.39 | 66.88 | 27.80 |
| 2.0 | 0.49 | 2.76 | 4.42 | 2.0 | 38.95 | 85.29 | 45.47 |
| 3.0 | 0.29 | 1.80 | 2.94 | 3.0 | 40.09 | 93.60 | 57.89 |
| 4.0 | 0.17 | 1.15 | 2.34 | 4.0 | 40.89 | 98.89 | 67.19 |
| 8.0 | 0.00 | 0.48 | 1.48 | 8.0 | 42.55 | 109.88 | 93.19 |
| 12.0 | | | 0.93 | 12.0 | | | 110.52 |
| 18.0 | | | 0.11 | 18.0 | | | 121.81 |

Example 8

Figure 9:
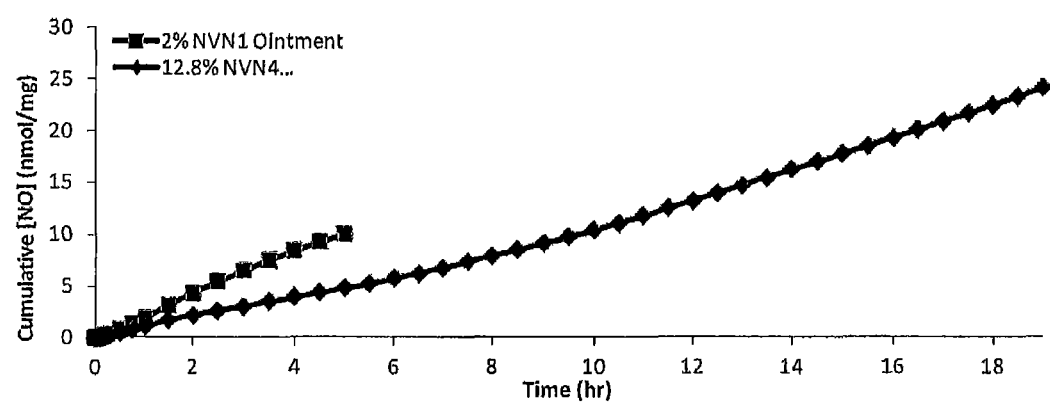
FIG. 9 shows a graph of the cumulative nitric oxide (NO) release over time for each of the two ointments.
Figure 10:
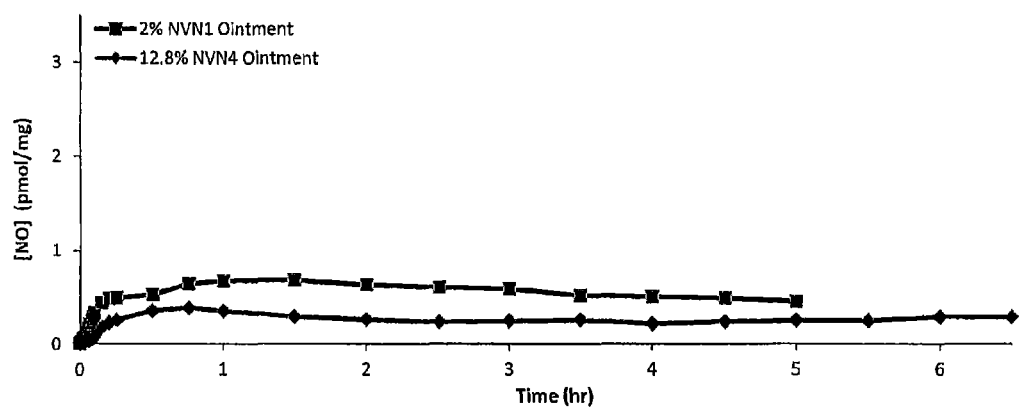
FIG. 10 shows a graph of the real time NO release over time for each of the two ointments.

The release of nitric oxide from two different ointments was compared. The ointment formulation was TO-007b, as provided in Table 12, containing either 12.8% Nitricil™ NVN4 (1.8% NO content) or 2% Nitricil™ NVN1 (0.3% NO content). The real time NO release and cumulative NO for the different ointments are provided in Table 13. The cumulative NO release over time for the admixtures is provided in FIG. 9 and the real-time concentration of NO release over time for the admixtures is provided in FIG. 10.

TABLE 12

Ointment formulations.

| | Ointment Formulations (TO-007b) | |
|---|---|---|
| Component | 2% Nitricil™ NVN1 | 12.8% Nitricil™ NVN4 |
| Crodabase SQ | 60.0 | 58.0 |
| Miglyol ® 812 | 12.0 | 12.0 |
| Hexylene glycol | 8.0 | 8.0 |
| Softigen ® 767 | 5.0 | 5.0 |
| Light Mineral Oil | 13.0 | 4.2 |
| Nitricil™ NVN1 | 2.0 | — |
| Nitricil™ NVN4 | — | 12.8 |
| Total | 100 | 100 |

TABLE 13

Ointment NO release properties.

| Time (hr) | Real-Time NO Release (pmol/mg) | | Time (hr) | Cumulative NO (nmol/mg) | |
|---|---|---|---|---|---|
| | 2% NVN1 | 12.8% NVN4 | | 2% NVN1 | 12.8% NVN4 |
| 0.50 | 0.53 | 0.35 | 0.50 | 0.75 | 0.40 |
| 1.00 | 0.67 | 0.35 | 1.00 | 1.86 | 1.06 |
| 2.00 | 0.63 | 0.26 | 2.00 | 4.29 | 2.17 |
| 3.00 | 0.59 | 0.24 | 3.00 | 6.48 | 3.03 |
| 4.00 | 0.50 | 0.21 | 4.00 | 8.38 | 3.92 |
| 8.00 | | 0.33 | 8.00 | | 7.89 |
| 12.00 | | 0.40 | 12.00 | | 13.26 |
| 18.00 | | 0.46 | 18.00 | | 22.51 |
| 21.50 | | 0.50 | 21.50 | | 28.54 |

Example 9

Topical compositions were prepared having a hydrophobic composition and a hydrophilic composition. The hydrophobic and hydrophilic compositions were separately stored in an airless dual-chamber pump and subsequently admixed to form the topical composition. The topical compositions are provided in Tables 14-16.

TABLE 14

Formulation for a topical composition having a hydrophobic composition and a hydrophilic composition.

| Ingredient | % w/w |
|---|---|
| Chamber A | |
| Petrolatum | 21.50 |
| Snow White Petrolatum, Penreco | |
| Petrolatum and Polyethylene | 21.50 |
| Crodabase SQ, Croda | |
| Medium Chain Triglyceride | 4.00 |
| Miglyol ® 812, Peter Cremer | |
| Mineral Oil | 2.00 |
| Drakeol, Penreco | |
| Macrogol 6 Glycerol Caprylocaprate | 1.00 |
| Softigen ® 767 | |
| Chamber B | |
| Purified Water | 43.55 |
| Decon, or equivalent | |
| Glycerin | 5.00 |
| Spectrum, or equivalent | |
| Carboxymethylcellulose Sodium | 1.40 |
| Aqualon CMC 7M8SF PH, Ashland | |

TABLE 14-continued

Formulation for a topical composition having a hydrophobic composition and a hydrophilic composition.

| Ingredient | % w/w |
|---|---|
| Benzoic Acid Spectrum, or equivalent | 0.05 |

TABLE 15

Topical compositions having a hydrophobic composition and a hydrophilic composition.

| | % w/w | | | |
|---|---|---|---|---|
| Component | Placebo | 0.05% | 0.5% | 5% |
| Chamber A | | | | |
| Petrolatum and polyethylene Crodabase SQ | 21.00 | 20.98 | 20.75 | 18.75 |
| White Petrolatum Super White Petrolatum USP | 21.00 | 20.97 | 20.75 | 18.75 |
| Medium chain triglycerides Miglyol ® 812 | 4.00 | 4.00 | 4.00 | 4.00 |
| Mineral oil Drakeol 34 USP | 2.00 | 2.00 | 2.00 | 1.50 |
| Caprylocaproyl polyoxylglycerides Softigen ® 767 | 2.00 | 2.00 | 2.00 | 2.00 |
| Nitricil ™ NVN1 Drug Substance | — | 0.05 | 0.50 | 5.00 |
| Chamber B | | | | |
| Glycerin | 5.00 | 5.00 | 5.00 | 5.00 |
| Potassium phosphate dibasic | — | 3.60 | 3.60 | — |
| Potassium phosphate monobasic | — | 2.90 | 2.90 | 5.90 |
| Sodium carboxymethylcellulose | 1.40 | 1.40 | 1.40 | 1.40 |
| Benzoic acid | 0.05 | 0.05 | 0.05 | 0.05 |
| Purified water | 43.55 | 37.05 | 37.05 | 37.65 |

TABLE 16

Topical compositions having a hydrophobic composition and a hydrophilic composition.

| | % w/w | | | |
|---|---|---|---|---|
| Component | Placebo | 0.07% | 0.7% | 7% |
| Chamber A | | | | |
| Petrolatum and polyethylene Crodabase SQ | 21.00 | 20.97 | 20.65 | 17.75 |
| White Petrolatum Super White Petrolatum USP | 21.00 | 20.96 | 20.65 | 17.75 |
| Medium chain triglycerides Miglyol ® 812 | 4.00 | 4.00 | 4.00 | 4.00 |
| Mineral oil Drakeol 34 USP | 2.00 | 2.00 | 2.00 | 1.50 |
| Caprylocaproyl polyoxylglycerides Softigen ® 767 | 2.00 | 2.00 | 2.00 | 2.00 |
| Nitricil ™ NVN4 Drug Substance | — | 0.07 | 0.70 | 7.00 |
| Chamber B | | | | |
| Glycerin | 5.00 | 5.00 | 5.00 | 5.00 |
| Potassium phosphate dibasic | — | 3.60 | 3.60 | — |
| Potassium phosphate monobasic | — | 2.90 | 2.90 | 5.90 |
| Sodium carboxymethylcellulose | 1.40 | 1.40 | 1.40 | 1.40 |
| Benzoic acid | 0.05 | 0.05 | 0.05 | 0.05 |
| Purified water | 43.55 | 37.05 | 37.05 | 37.65 |

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A topical composition comprising a hydrophilic composition and a hydrophobic composition in admixture; wherein the hydrophilic composition is a hydrogel and comprises a polymer, polyhydric alcohol, and water, wherein water is present in an amount of about 50% to about 99% by weight of the hydrophilic composition; wherein the hydrophobic composition comprises an active pharmaceutical ingredient, at least one hydrophobic base and at least one amphiphilic compound and/or emulsifying agent, wherein the active pharmaceutical ingredient comprises a diazeniumdiolate functionalized macromolecule; and wherein the topical composition is self-emulsifying and is an emulsion.

2. The topical composition of claim 1, wherein the polymer is a cellulose or a pharmaceutically acceptable salt thereof, chitosan, an acrylic acid polymer, or any combination thereof.

3. The topical composition of claim 1, wherein the polyhydric alcohol is present at a concentration from about 5% to about 20% by weight of the hydrophilic composition, and the polymer is present at a concentration from about 0.5% to about 10% by weight of the hydrophilic composition.

4. The topical composition of claim 1, wherein the hydrophilic composition has a viscosity of about 5000 cP to about 100,000 cP.

5. The topical composition of claim 1, wherein the topical composition is continuous.

6. The topical composition of claim 1, wherein the topical composition has a pH of about 3 to about 9.

7. The topical composition of claim 1, wherein the diazeniumdiolate functionalized macromolecule comprises a NO-releasing co-condensed silica particle.

8. The topical composition of claim 1, wherein the hydrophilic composition comprises a buffer.

9. The topical composition of claim 1, further comprising: a cosolvent.

10. The topical composition of claim 9, wherein the hydrophobic composition comprises the cosolvent.

11. The topical composition of claim 10, wherein the hydrophobic composition comprises at least two hydrophobic bases.

12. The topical composition of claim 10, wherein the hydrophobic composition comprises:
the at least one hydrophobic base at a concentration from about 25% to about 98% by weight of the hydrophobic composition;
the at least one amphiphilic compound and/or emulsifying agent at a concentration from about 0.5% to about 10% by weight of the hydrophobic composition; and
the cosolvent at a concentration from about 1% to about 20% by weight of the hydrophobic composition; and
wherein the hydrophilic composition comprises:
the polymer at a concentration from about 0.5% to about 10% by weight of the hydrophilic composition; and
the polyhydric alcohol at a concentration from about 5% to about 20% by weight of the hydrophilic composition.

13. A kit comprising:
a first composition comprising a hydrophilic composition; and a second composition comprising a hydrophobic composition, wherein the hydrophilic composition comprises a cellulose or a pharmaceutically acceptable salt thereof, a polyhydric alcohol, and water, wherein water is present in the hydrophilic composition in an amount of about 50% to about 99% by weight of the hydrophilic composition, and wherein the hydrophobic composition comprises an active pharmaceutical ingredient, an amphiphilic compound, and at least one hydrophobic base, and wherein the active pharmaceutical ingredient comprises a diazeniumdiolate functionalized macromolecule.

14. The kit of claim 13, wherein the hydrophilic composition has a pH of about 4 to about 8.

15. The kit of claim 13, wherein the first composition and second composition are separately stored.

16. The topical composition of claim 8, wherein the buffer is a phosphate buffer.

17. The topical composition of claim 8, wherein the buffer comprises acetic acid and an acetate.

18. The topical composition of claim 9, wherein the cosolvent is a mineral oil.

19. The topical composition of claim 1, wherein the topical composition is a continuous emulsion that remains as a single phase for at least 2 days.

20. The topical composition of claim 1, wherein the ratio of hydrophilic composition to hydrophobic composition is about 1:1, 2:1, or 3:1.

21. The topical composition of claim 1, wherein the ratio of hydrophilic composition to hydrophobic composition is about 1:1.

22. The topical composition of claim 1, wherein the diazeniumdiolate functionalized macromolecule is present in the hydrophobic composition at a concentration from about 0.01% to about 30% by weight of the hydrophobic composition.

* * * * *